US010709556B2

(12) United States Patent
Griffin et al.

(10) Patent No.: US 10,709,556 B2
(45) Date of Patent: Jul. 14, 2020

(54) TRANSCATHETER PROSTHESIS WITH SEALING COMPONENT, AND SYSTEMS AND METHODS FOR DELIVERING AND DEPLOYMENT THEREOF

(71) Applicant: Medtronic Vascular, Inc., Santa Rosa, CA (US)

(72) Inventors: Patrick Griffin, Galway (IE); James R. Keogh, Maplewood, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 185 days.

(21) Appl. No.: 15/685,231

(22) Filed: Aug. 24, 2017

(65) Prior Publication Data

US 2019/0060063 A1  Feb. 28, 2019

(51) Int. Cl.
*A61F 2/24*  (2006.01)
*A61F 2/95*  (2013.01)
*A61F 2/848*  (2013.01)

(52) U.S. Cl.
CPC .......... *A61F 2/2418* (2013.01); *A61F 2/2427* (2013.01); *A61F 2/2439* (2013.01); *A61F 2/95* (2013.01); *A61F 2/243* (2013.01); *A61F 2/848* (2013.01); *A61F 2002/9511* (2013.01); *A61F 2002/9522* (2013.01); *A61F 2002/9528* (2013.01); *A61F 2250/0069* (2013.01)

(58) Field of Classification Search
CPC ...... A61F 2002/9511; A61F 2002/6522; A61F 2002/9528; A61F 2/9241; A61F 2250/0069

See application file for complete search history.

(56) References Cited

U.S. PATENT DOCUMENTS

| 5,554,183 | A | * | 9/1996 | Nazari | ...................... A61F 2/07 623/1.13 |
| 6,053,943 | A | | 4/2000 | Edwin et al. | |
| 6,319,276 | B1 | * | 11/2001 | Holman | ........... A61B 17/12045 623/1.11 |
| 6,663,664 | B1 | | 12/2003 | Pacetti | |

(Continued)

OTHER PUBLICATIONS

PCT International Search Report and Opinion dated Nov. 2, 2018.

*Primary Examiner* — Diane D Yabut
(74) *Attorney, Agent, or Firm* — Medler Ferro Woodhouse & Mills PLLC

(57) ABSTRACT

A transcatheter prosthesis with radially compressed and expanded configurations. An elongate member encircling at least a portion of the prosthesis, and configured to provide a seal between the prosthesis and a native anatomy when the prosthesis is deployed in the radially expanded configuration. The elongate member may be a resilient elongate member having a radially contracted state, when in tension, to hold at least the portion of the prosthesis in the radially compressed configuration, and having a radially expanded state, when relaxed, to provide the seal between at least the portion of the prosthesis and a native anatomy when the prosthesis is deployed. A system for delivering the transcatheter prosthesis may include a delivery catheter having an elongate cinching member encircling at least a second portion of the prosthesis, wherein the elongate cinching member is configured to hold the second portion of the prosthesis in the radially compressed configuration.

19 Claims, 21 Drawing Sheets

(56) References Cited

U.S. PATENT DOCUMENTS

| | | |
|---|---|---|
| 7,662,186 B2 | 2/2010 | Bragga et al. |
| 7,740,655 B2 | 6/2010 | Birdsall |
| 8,512,401 B2 | 8/2013 | Murray, III et al. |
| 8,579,963 B2 | 11/2013 | Tabor |
| 8,852,271 B2 | 10/2014 | Murray, III et al. |
| 8,876,893 B2 | 11/2014 | Dwork |
| 8,926,692 B2 | 1/2015 | Dwork |
| 8,998,980 B2 | 4/2015 | Shipley et al. |
| 2007/0100427 A1* | 5/2007 | Perouse .................. A61F 2/07 623/1.11 |
| 2008/0288047 A1 | 11/2008 | Friebe |
| 2010/0016943 A1 | 1/2010 | Chobotov |
| 2011/0093060 A1 | 4/2011 | Cartledge |
| 2014/0330368 A1 | 11/2014 | Gloss et al. |
| 2015/0272756 A1 | 10/2015 | Cartledge |
| 2017/0172724 A1 | 6/2017 | Cartledge et al. |

\* cited by examiner

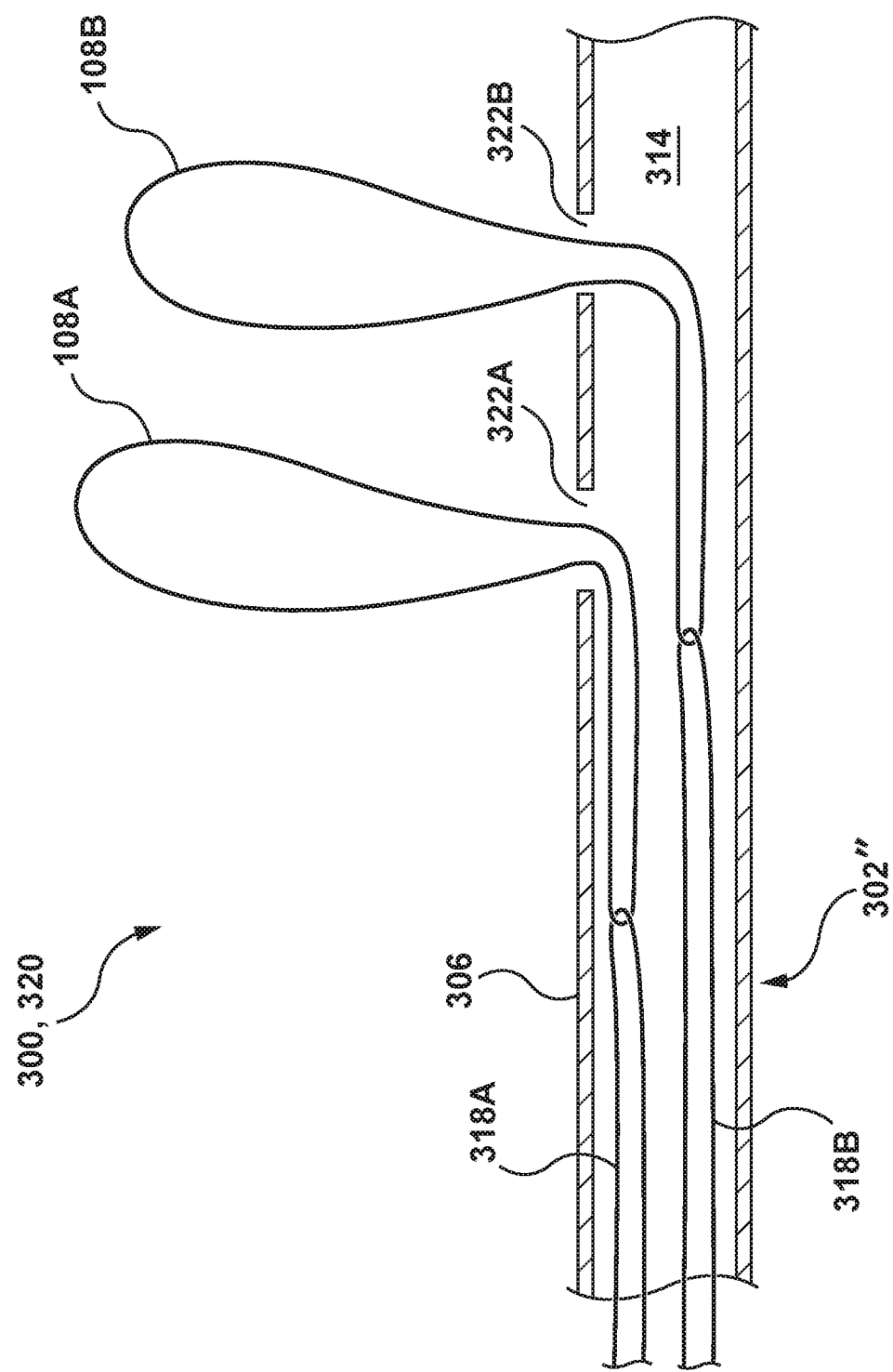

US 10,709,556 B2

TRANSCATHETER PROSTHESIS WITH SEALING COMPONENT, AND SYSTEMS AND METHODS FOR DELIVERING AND DEPLOYMENT THEREOF

FIELD OF THE INVENTION

The invention relates generally to prostheses for intervascular delivery and associated systems and methods. More particularly, the present invention relates to valve prostheses with sealing components to prevent paravalvular leakage after deployment of the valve prostheses, and systems and methods associated therewith.

BACKGROUND OF THE INVENTION

The human heart is a four chambered, muscular organ that provides blood circulation through the body during a cardiac cycle. The four main chambers include the right atria and right ventricle which supplies the pulmonary circulation, and the left atria and left ventricle which supplies oxygenated blood received from the lungs to the remaining body. To ensure that blood flows in one direction through the heart, atrioventricular valves (tricuspid and mitral valves) are present between the junctions of the atria and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream direction.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such valve prostheses can be percutaneously delivered while in a low-profile or radially compressed configuration so that the valve prosthesis can be advanced through the patient's vasculature and deployed at the site of the diseased heart valve through catheter-based systems. Once positioned at the treatment site, the valve prosthesis can be expanded to engage tissue at the diseased heart valve region to, for instance, hold the valve prosthesis in position.

However, in some patients, the valve prosthesis may not perform as desired following implantation. For example, the valve prosthesis may not fully seal with the native anatomy at an implantation site of the native valve, resulting in paravalvular leakage (PVL), which can be a serious post-surgical complication.

Accordingly, there is a need for systems and components to minimize the crossing profile of a delivery catheter and provide sealing of a valve prosthesis with the native anatomy.

BRIEF SUMMARY OF THE INVENTION

Embodiments hereof are directed to a transcatheter prosthesis system including a transcatheter prosthesis and a delivery catheter. The transcatheter prosthesis has a radially compressed configuration for delivery within a vasculature and a radially expanded configuration for deployment within a native anatomy. The transcatheter prosthesis includes a frame and an elongate member. The elongate member encircles at least a portion of the frame and provides a seal between the prosthesis and the native anatomy when the prosthesis is in the radially expanded configuration, and may be an elongate resilient member or an elongate sealing member. The delivery catheter includes an elongate cinching member encircling at least a portion of the frame. The elongate cinching member is configured to hold the prosthesis in the radially compressed configuration.

Embodiments hereof are also directed to a transcatheter prosthesis including a frame, a fixation member and an elongate member. The transcatheter prosthesis has a radially compressed configuration for delivery within a vasculature and a radially expanded configuration for deployment within a native anatomy. The fixation member is coupled to and configured to extend outwardly from an outer surface of the frame. The elongate member encircles at least a portion of the frame. The elongate member, which may be an elongate resilient member or an elongate sealing member, is slidably disposed within the fixation member and provides a seal between the prosthesis in the radially expanded configuration and the native anatomy.

Embodiments hereof are also directed to a method of deploying and sealing a prosthesis within a native anatomy. A prosthesis with an elongate member is loaded onto a delivery catheter, wherein the elongate member encircles at least a portion of a frame of the prosthesis and provides a seal between the prosthesis and the native anatomy when the prosthesis is in a radially expanded configuration. The prosthesis is deployed in the radially expanded configuration at the native anatomy, wherein the elongate member seals between the prosthesis and the native anatomy to prevent blood flow therebetween.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1AA depicts a cross-sectional view of a resilient elongate member in a radially contracted state, taken along line AA-AA of FIG. 1A.

FIG. 3AA depicts a side view of the resilient elongate member of FIG. 3A in a tensioned or contracted state according to an embodiment hereof.

FIG. 3BB depicts an end view of the resilient elongate member of FIG. 3AA in the tensioned or contracted state according to an embodiment hereof.

FIG. 7A depicts a sectional view of a distal portion of the delivery catheter of FIG. 6A with a tensioning mechanism and two resilient elongate members according to another embodiment hereof.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of embodiments hereof are in the context of treatment of heart valves, such as the aortic or mitral valve, and aortic aneurysms, such as with a stent-graft, the invention may also be used in any other valve locations and body passageways where it is deemed useful. Furthermore, there is no intention to be bound by any expressed or implied theory presented in the preceding technical field, background, brief summary or the following detailed description.

Figure 1:
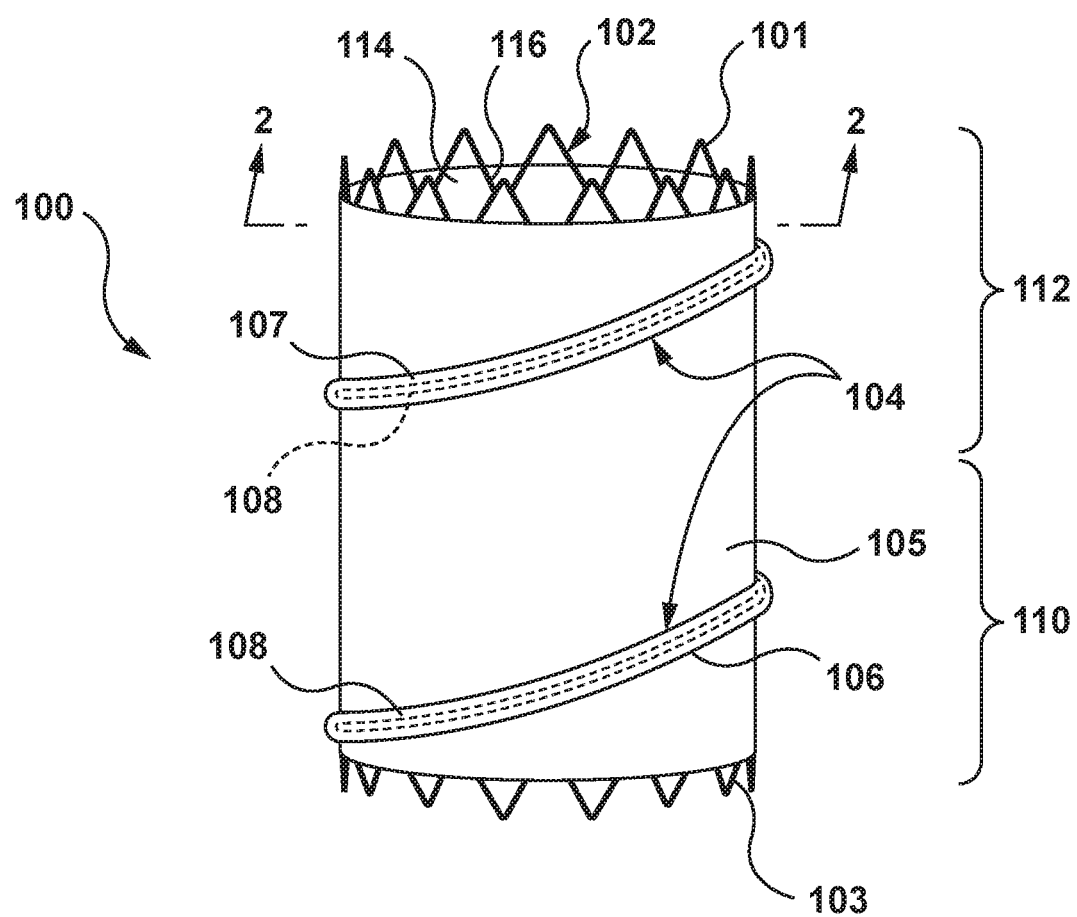
FIG. 1 depicts a prosthesis with a cinching and sealing component according to an embodiment hereof, wherein the prosthesis is in a radially expanded configuration.
Figure 1A:
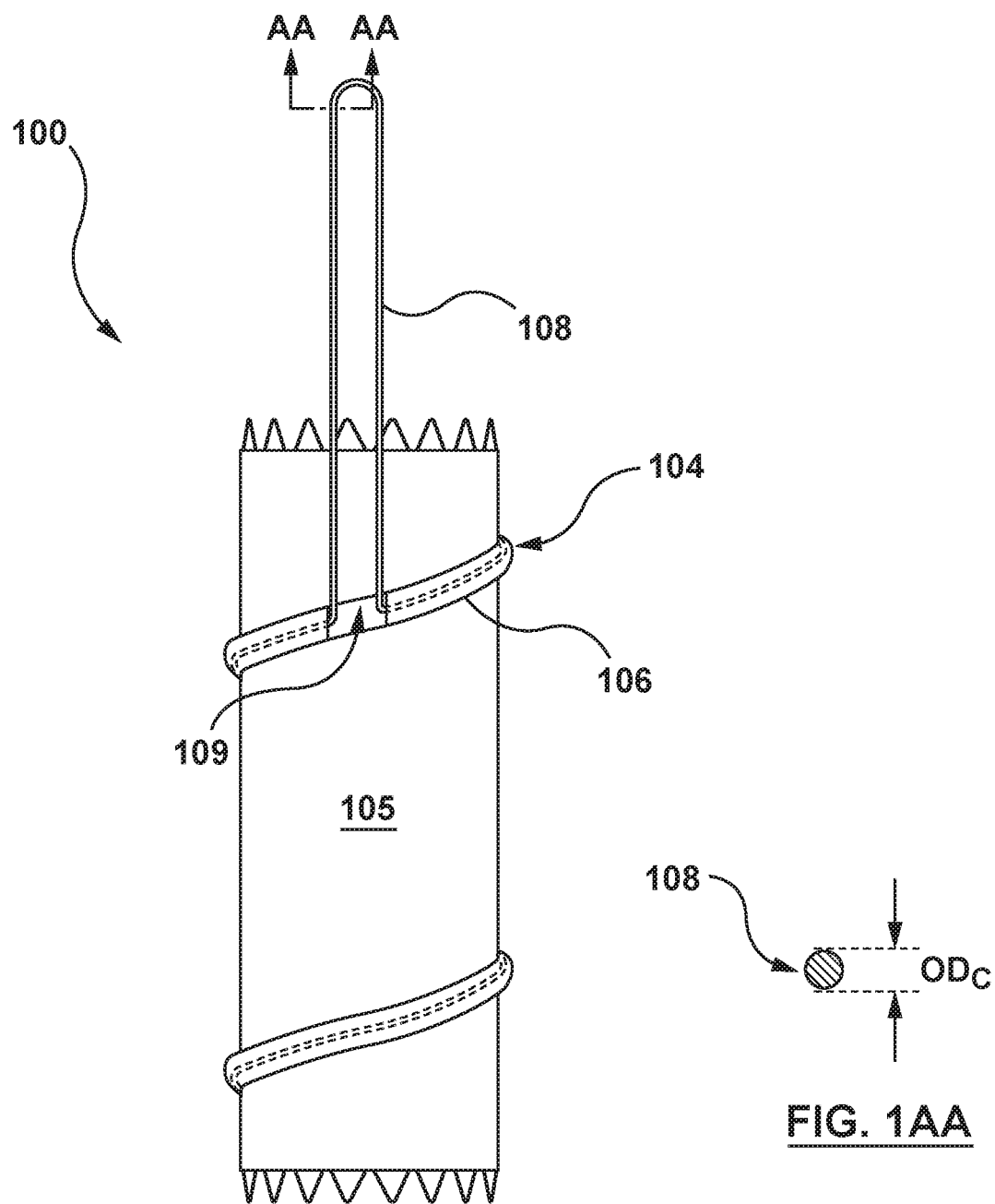
FIG. 1A depicts the prosthesis of FIG. 1 in a radially compressed configuration with the cinching and sealing component in tension in accordance with an embodiment hereof.

In an embodiment in accordance herewith shown in FIG. 1, a transcatheter prosthesis 100 (hereafter referred to as prosthesis 100) includes a frame 102, an outer layer component 105 encircling at least a portion of the frame 102, and a sealing component 2042 figured to provide a seal between the prosthesis 100 and the native anatomy. The prosthesis 100 may be manipulated into a radially compressed configuration for delivery, as shown in FIG. 1A, and thereafter may return to a radially expanded configuration, as shown in FIG. 1, when deployed at a desired treatment location. The sealing component 104 includes a fixation member 106 and an elongate member 108, which is more clearly shown in FIG. 2. In some embodiments, the sealing component 104 also acts as a cinching component, e.g. the cinching and sealing component 104 is configured to hold the prosthesis 100 in the radially compressed configuration for delivery to the desired treatment location and is further configured to provide a seal between the prosthesis 100 and the native anatomy. In some embodiments, the elongate member 108 is a resilient elongate member 108. In some embodiments, when the resilient elongate member 108 is in a radially contracted state, the resilient elongate member 108 of the cinching and sealing component 104 is configured to hold the prosthesis 100 in the radially compressed configuration for delivery to the desired treatment location. In some embodiments, when the resilient elongate member 108 is in a radially expanded state, which permits the prosthesis 100 to return to the radially expanded configuration, the cinching and sealing component 104 is further configured to provide a seal between the prosthesis 100 and the native anatomy.

As referred to herein, the prosthesis 100 may assume a wide variety of configurations. The prosthesis 100 may include a bioprosthetic heart valve having tissue leaflets or a synthetic heart valve having polymeric, metallic or tissueengineered leaflets, and can be specifically configured for replacing valves of the human heart. The prosthesis 100 of the present disclosure may be self-expandable, balloon expandable and/or mechanically expandable or combinations thereof. In general terms, the prosthesis 100 of the present disclosure may include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthesis 100. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., Nitinol™). The stent frame can be laser-cut from a single piece of material, or can be assembled from a number of discrete components.

If provided, a valve structure of the prosthesis 100 can assume a variety of forms, and can be formed, for example, from one or more biocompatible synthetic materials, synthetic polymers, autograft tissue, homograft tissue, xenograft tissue, or one or more other suitable materials. In some embodiments, the valve structure can be formed, for example, from bovine, porcine, equine, ovine and/or other suitable animal tissues. In some embodiments, the valve structure is formed, for example, from heart valve tissue, pericardium, and/or other suitable tissue. In some embodiments, the valve structure can include or form one or more leaflets 36. For example, the valve structure can be in the form of a tri-leaflet bovine pericardium valve, a bi-leaflet valve, or another suitable valve.

In various embodiments hereof, the frame 102 is self-expanding to return to a radially expanded configuration from a radially compressed configuration. The frame 102 may include an inflow section 110 and an outflow section 112, as shown in FIG. 1. The frame 102 further may be described as having a stent-like support structure comprised of a plurality of cells 114 formed by a plurality of struts 116. Depending on the intended application of the prosthesis 100, the plurality of cells 114 may have sizes that vary along the length of the frame 102, or may have the same size and shape along the length of the frame 102. The frame 102 may be formed of any suitable biocompatible material in which a mechanical or shape memory may be imparted including, but not limited to stainless steel, nickel-titanium alloys (e.g. NITINOL), and certain polymeric materials. "Self-expanding" as used herein means that a structure has been formed or processed to have a mechanical or shape memory to return to the radially expanded configuration. Mechanical or shape memory may be imparted to the structure that forms the frame 102 using techniques understood in the art.

Figure 2:
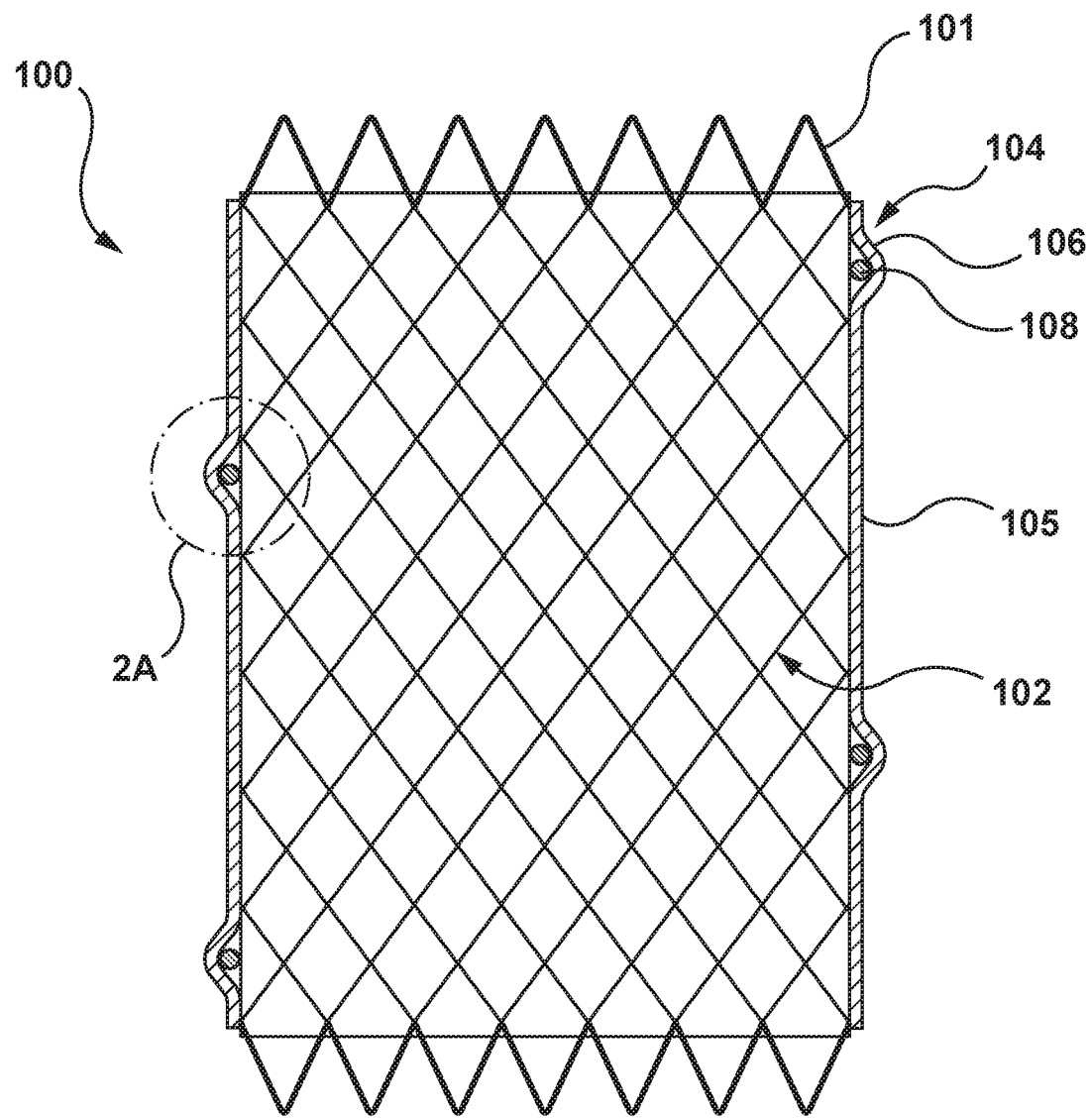
FIG. 2 depicts a longitudinal-sectional view of the prosthesis taken at line 2-2 of FIG. 1.

As also shown in FIGS. 1 and 2, the outer layer 105 of the prosthesis 100 may be a flexible and/or non-permeable sheet of material that is attached to the frame 102 to encircle at least a portion of an outer surface thereof. In some embodiments, the outer layer 105 may be a sealing skirt of a heart valve prosthesis. The outer layer 105 may be constructed of one or more suitable biocompatible materials, non-limiting examples of which include synthetic materials, synthetic polymers, polyester, nylon, expanded polytetrafluoroethylene (ePTFE), natural tissue (e.g. porcine, equine, or bovine pericardium), autograft tissue, homograft tissue, xenograft tissue, or other materials suitable for the purposes described herein. A heart valve prosthesis may comprise two or three leaflets that are fastened together at enlarged lateral end regions to form commissural joints, with the unattached edges forming coaptation edges of the valve structure. The leaflets may be fastened to the outer layer 105 that in turn is attached or coupled to the frame 102. The outer layer 105 may be coupled to the frame 102 by methods such as, but not limited to fusing, welding, gluing, or sewing. Although the embodiment of FIGS. 1 and 2 show the outer layer 105 extending about an entire circumference of the frame 102, and generally extending from a first end 101 to a second end 103 of the frame 102, in other embodiments the outer layer 105 may extend about only a portion of the circumference and/or a greater or lesser length of the frame 102, such as extending over only the inflow section 110 or outflow section 112, or portions thereof. In some embodiments, prosthesis 100 may not comprise an outer layer 105.

Figure 2A:
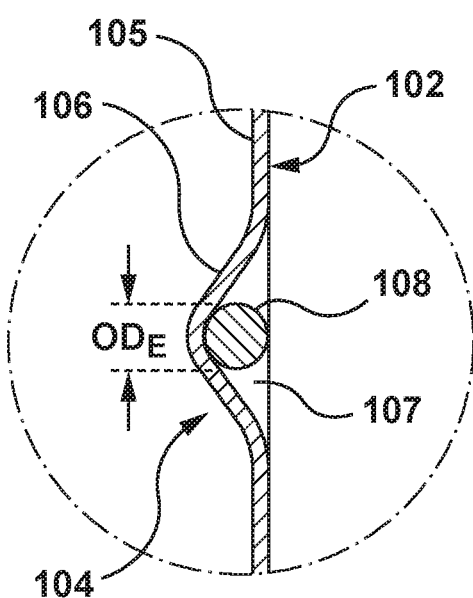
FIG. 2A depicts an enlarged area 2A of FIG. 2 depicting a resilient elongate member in a radially expanded state.

In some embodiments, as shown in FIGS. 1 and 2, the fixation member 106 is a curved projection, or fold, either formed in the outer layer 105 or attached or coupled to the outer layer 105 and/or the frame 102 that extends outwardly from an outer surface of the frame 102. In an embodiment, the fixation member 106 may be configured to encircle at least a portion of the outer surface of the frame 102. The fixation member 106, as best shown in FIGS. 2 and 2A, may be described as defining a channel 107 that is sized to slidably receive the resilient elongate member 108 therein. In an embodiment, as shown in FIGS. 1, 2, 2A and 4, the fixation member 106, i.e., the curved projection, or fold, formed in the outer layer 105 or attached or coupled to the outer layer 105 and/or the frame 102, may define a continuous channel 107 having a helical path around the outer surface of the frame 102 such that the corresponding resilient elongate member 108 received therein forms a generally helical path about the outer surface of the frame 102. In another embodiment, the fixation member 106, i.e., the curved projection, or fold, formed in the outer layer 105 or attached or coupled to the outer layer 105 and/or the frame 102, may define a continuous or non-continuous channel 107 having a circular path around the outer surface of the frame 102 such that the corresponding resilient elongate member 108 received therein forms a generally circular path about the outer surface of the frame 102.

The elongate member 108 is threaded or routed though the channel 107 of the fixation member 106 to encircle the frame 102 of the prosthesis 100, and has ends that are secured to each other to form a loop, as shown in FIG. 1A. In one embodiment, the elongate member 108 is a resilient elongate member 108 which includes a radially contracted state when the resilient elongate member 108 is in tension, as shown in FIGS. 1A and 1AA, and a radially expanded configuration when relaxed, as shown in FIGS. 1, 2 and 2A. When in tension in the radially contracted state, the resilient elongate member 108 has a contracted outer diameter $OD_C$, and axially elongates, as shown in FIG. 1A, to extend from an opening in or access port 109 of the fixation member 106, and thereby to extend from the prosthesis 100. In the radially contracted state, the resilient elongate member 108 may be tightened around the frame 102 to compress the frame into a radially compressed configuration and is configured to hold the prosthesis 100 in the radially compressed configuration for delivery to the desired treatment location. When the resilient elongate member 108 is relaxed, the resilient elongate member transitions to the radially expanded state to have an expanded outer diameter $OD_E$, and axially shortens, as shown in FIG. 1, to extend only within the fixation member 106. In the radially expanded state, or relaxed state, the resilient elongate member 108 is configured to both controllably release the frame 102 of the prosthesis 100 from the radially compressed configuration to the radially expanded configuration, and to substantially fill the channel 107 of the fixation member 106. The resilient elongate member 108 in the relaxed, radially expanded state thereby outwardly extends, pushes, or supports the fixation member 106, as shown in FIG. 2A, such that the cinching and sealing component 104, including the fixation member 106 with the resilient elongate member 108 disposed therein, provides a seal between the prosthesis 100 and the native anatomy when the prosthesis 100 is in the radially expanded configuration. Thus, in at least one embodiment, the resilient elongate member 108 of the cinching and sealing component 104 serves a dual purpose to both hold the prosthesis 100 in the radially compressed configuration for delivery to the desired treatment location and to seal and help prevent leakage between the prosthesis 100 and the native anatomy when the prosthesis 100 is deployed at the desired treatment location.

In an embodiment, a first end, portion or segment of the loop of the resilient elongate member 108 is coupled to the frame 102 or outer layer 105 such that tension may be applied on the resilient elongate member 108 to transition the resilient elongate member 108 from the radially expanded state to radially contracted state. The first end, portion or segment of the loop of the resilient elongate member 108 may be coupled to the frame 102 or outer layer 105 by methods including, but not limited to tying, fusing, welding, sutures, gluing, fastening, or other suitable methods.

Figures 3A, 3B:
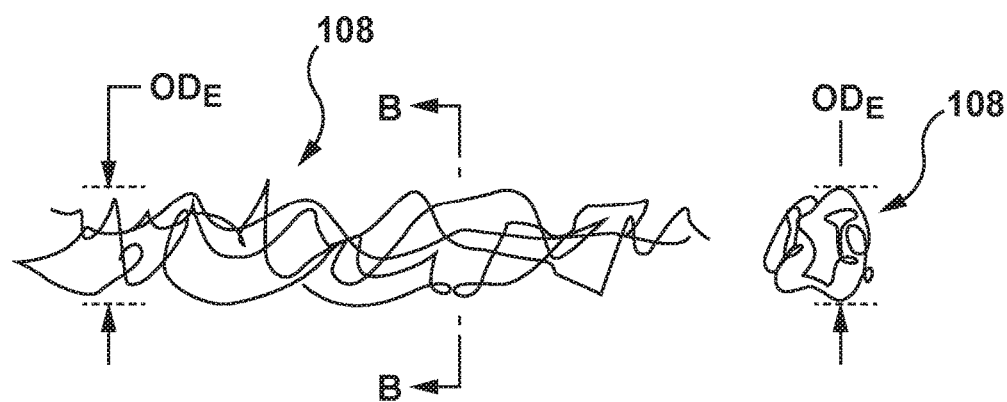
FIG. 3A depicts a side view of a resilient elongate member.
FIG. 3B depicts an end view of the resilient elongate member of FIG. 3A in the relaxed or expanded state according to an embodiment hereof.
Figures 3A, 3B:
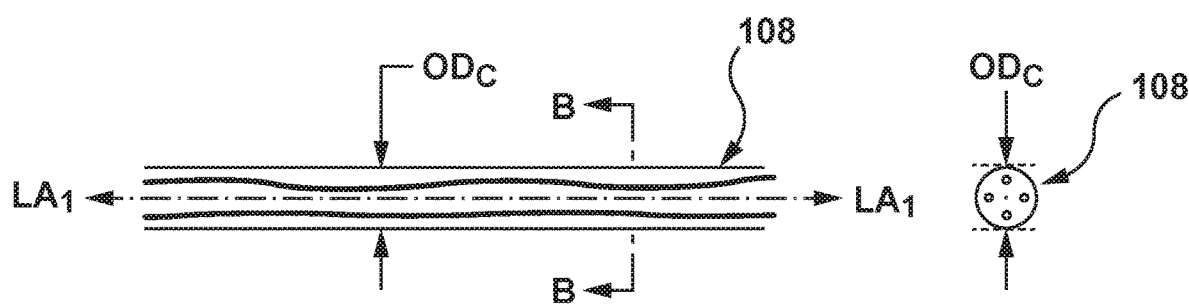

The elongate member 108 may be formed of one or more biocompatible materials such as, but not limited to, metals, e.g. stainless steel, nickel-titanium alloys (e.g. NITINOL), polymers, e.g. nylon, polybutester, polypropylene, silk, polyester, or other materials suitable for the purposes described herein. The resilient elongate member 108 may be formed of one or more elastic and/or shape memory materials. The elongate member 108 may comprise one or more sutures, cords, wires, fibers, or filaments. In an embodiment hereof, the resilient elongate member 108 may be a fibrous multifilar-bunched member that when relaxed/released will axially shorten and radially expand to the radially expanded state having an expanded outer diameter $OD_E$. Conversely, when under tension, the resilient elongate member 108 will axially lengthen but radially contract to the radially contracted state to have a contracted outer diameter $OD_C$. In an embodiment, as shown in FIGS. 3A and 3B, the resilient elongate member 108 may be a loose spinning of multiple individual shape memory fibers with a first thickness or expanded outer diameter $OD_E$. When tensioned, as shown in FIGS. 3AA and 3BB, the individual fibers of the fibrous multifilar-bunched resilient elongate member 108 are configured to substantially axially align, contracting or pulling towards a central longitudinal axis LA1 of the resilient elongate member 108 to radially contract the member to a second thickness or a contracted outer diameter $OD_C$.

Figure 3C:
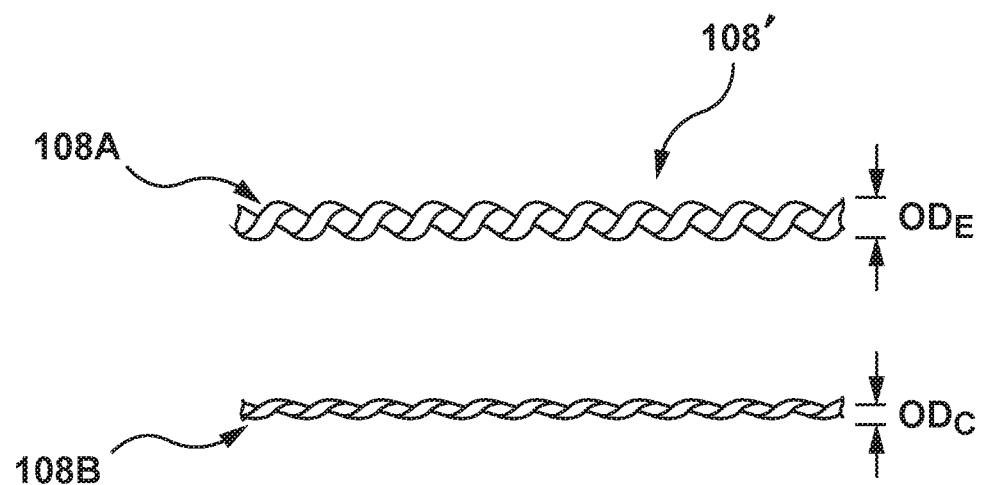
FIGS. 3C and 3D depicts a resilient elongate member according to other embodiments hereof.

In another embodiment shown in FIG. 3C, a resilient elongate member 108' is a braided material comprising one or more fibers that are spirally wrapped around a central core of one or more elastic fibers. When relaxed, the braided wrap allows the elastic core fibers to axially shorten or reduce in length and radially expand to the radially expanded state having an expanded outer diameter $OD_E$ shown by resilient elongate member 108A. When placed under tension, the braided spiral wrap becomes taut and squeezes the elastic core thereby axially stretching or lengthening the resilient elongate member 108' and radially contracting it to the radially contracted state having a contracted outer diameter $OD_C$ shown by resilient elongate member 108B.

Figure 3D:
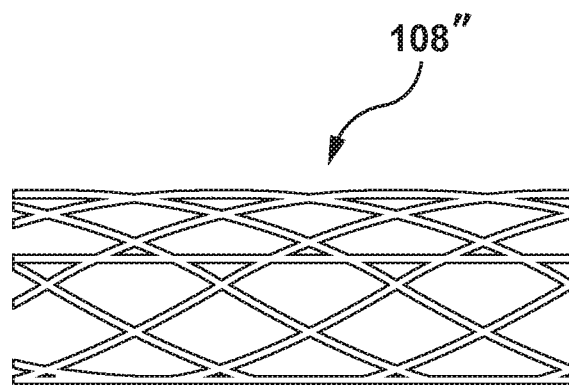

In another embodiment shown in FIG. 3D, a resilient elongate member 108" is a tubular structure created from a woven braid or mesh of shape memory material. When relaxed, the resilient elongate member 108" allows for axial shortening and radial expansion to the radially expanded state an expanded outer diameter $OD_E$, as shown in FIG. 3D. When the resilient elongate member 108" is placed in tension, the resilient elongate member 108" axially lengthens and radially contracts to the radially contracted state.

Figure 4:
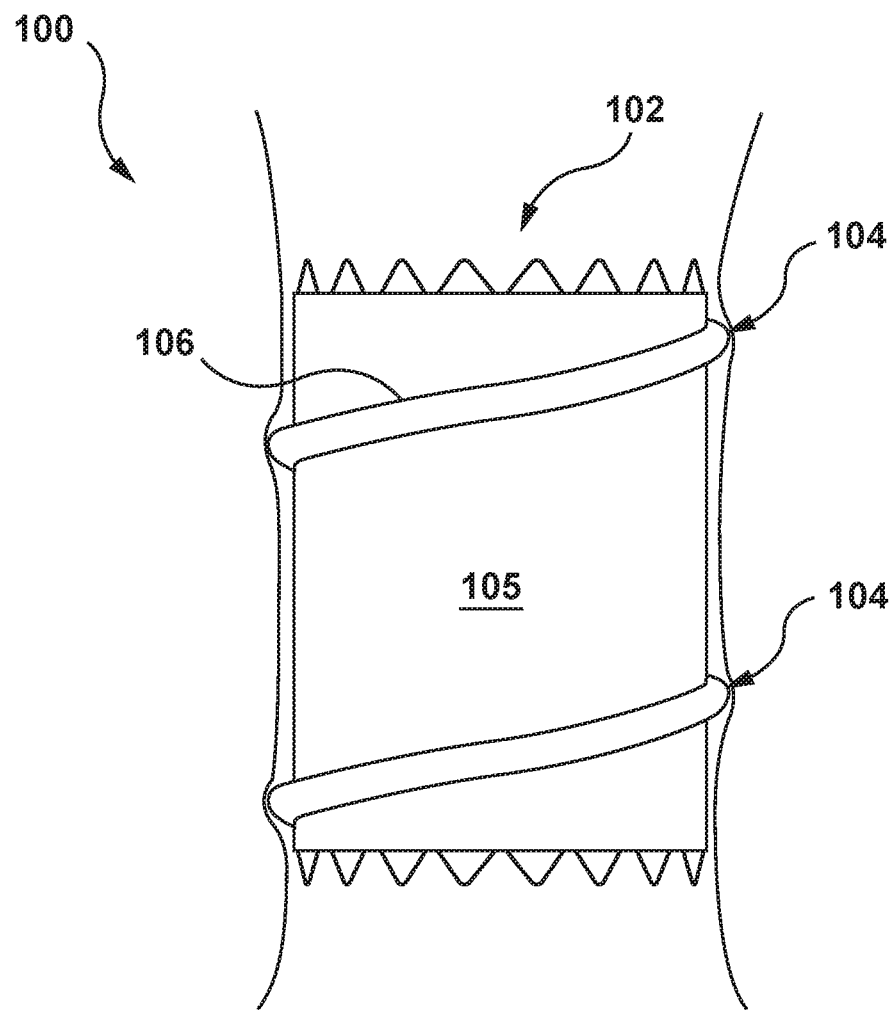
FIG. 4 depicts a schematic sectional illustration of the prosthesis of FIG. 1 implanted within a vessel.

With an understanding of the components of the prosthesis 100, the interaction of the various components is now described as to: holding the prosthesis 100 in the radially compressed configuration for delivery to a desired treatment location, controllably releasing the prosthesis 100 at the desired treatment location, and providing a seal between the prosthesis 100 and the native anatomy at the desired treatment location with the prosthesis 100 in the radially expanded configuration. In an embodiment, initially tension is placed on the resilient elongate member 108, such as by fixing the prosthesis 100 to a delivery device and then pulling on the resilient elongate member 108. With the resilient elongate member 108 in tension, the resilient elongate member 108 axially elongates and radially contracts and thereby compresses at least a portion of the frame 102 of the prosthesis 100 to transition at least a portion of the prosthesis to the radially compressed configuration of FIG. 1A for delivery to a desired treatment location. Once positioned at the desired treatment location, tension on the resilient elongate member 108 is released to permit controllable expansion of the frame 102 of the prosthesis 100 to permit the prosthesis to return to the radially expanded configuration of FIG. 1. The resilient elongate member 108 further transitions to the radially expanded state and substantially fills the channel 107 of the fixation member 106. As the channel 107 of the fixation member 106 is filled by the radially expanded resilient elongate member 108, the fixation member 106 extends outward. Thus, the sealing component 104 including the fixation member 106 with the resilient elongate member 108 disposed therein in the radially expanded state provides a seal between the prosthesis 100 and the native anatomy when the prosthesis 100 is in the radially expanded configuration, as shown in FIG. 4.

Figure 5:
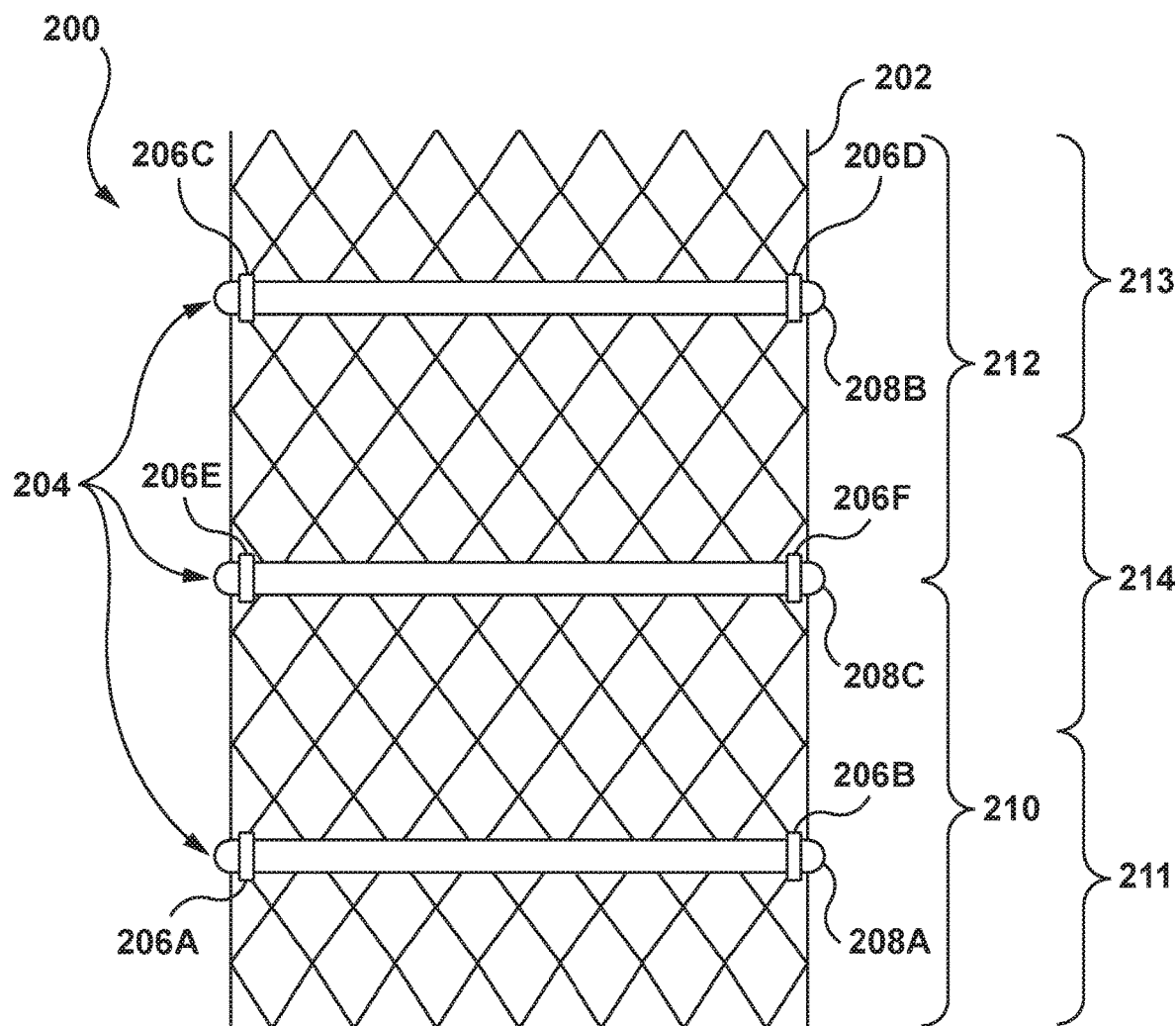
FIG. 5 depicts a prosthesis with a cinching and sealing component according to another embodiment hereof, wherein prosthesis is in a radially expanded configuration.

In another embodiment hereof, a transcatheter prosthesis 200 (hereafter referred to as prosthesis 200) includes a frame or stent-like support structure 202 and a cinching and sealing component 204, as shown in FIG. 5. The cinching and sealing component 204 includes a plurality of fixation members, such as fixation members 206A, 206B, 206C, 206D, 206E, 206F (hereafter referred to as fixation members 206A-206F or fixation member 206 for simplicity) and a plurality of resilient elongate members 208A, 208B, 208C (hereafter referred to as resilient elongate members 208A-208C or resilient elongate member 208 for simplicity). The prosthesis 200, the frame 202, and the resilient elongate member 208 of the cinching and sealing component 204 are substantially similar to the prosthesis 100, the frame 102, and the resilient elongate member 108 of the cinching and sealing component 104 previously described. Therefore, similar construction and alternatives of those features will not be repeated, and only new or modified features pertaining to the embodiment of FIG. 5 will be described in detail.

In the embodiment of FIG. 5, the cinching and sealing component 204 includes six (6) fixation members 206A-

206F and three (3) resilient elongate members 208A-208C but more or fewer of each may be incorporated without departing from the scope hereof. Each fixation member 206A-206F is coupled to the frame 202 and configured to form a channel, loop or ring extending outwardly from an outer surface of the frame 202. Each fixation member 206A-206F is configured with sufficient looseness, similar to a belt loop on a pair of pants for instance, to slidably receive the corresponding resilient elongate member 208A-208C. In the embodiment of FIG. 5, a pair of fixations members, such as fixation members 206A, 206B, fixation members 206C, 206D, or fixation members 206E, 206F are spaced apart about a circumference of the frame and a corresponding resilient elongate member 208A, 208B, 208C, respectively, is disposed within the corresponding pair of fixation members. In an embodiment, a plurality of fixation members, i.e., two, three, four, five or more fixation members, may be aligned and spaced apart from each other about a circumferences of the frame 202 at the same longitudinal position of the frame, such that the corresponding resilient elongate member received therein forms a generally circular path about the outer circumference of the frame 202.

In an embodiment, each fixation member 206A-206F may be a loop, suture, fold, strip or band of a biocompatible material, as described above, either attached or coupled to an outer layer and/or the frame 202, or formed from an outer layer, as described earlier. In another embodiment, each fixation member 206A-206F may be one or more loops, sutures, folds, strips or bands of a material such as, but not limited to synthetic materials, synthetic polymers, natural polymers, nylon, ePTFE, polybutester, polypropylene, silk, polyester, animal tissue (e.g. porcine, equine, or bovine pericardium), autograft tissue, homograft tissue, xenograft tissue, shape memory materials, metals, stainless steel, nickel-titanium alloys (e.g. NITINOL), or other materials suitable for the purposes described herein. Each fixation member 206A-206F may be coupled to an outer layer, as described earlier, and/or the frame 202 by a variety of methods, non-limiting examples of which include sewing, fusing, welding, gluing, fastening, or otherwise tied. In another embodiment, each fixation member 206A-206F may be formed from or include a portion of the frame 202. In accordance with embodiments hereof, fixation members 206A-206F, which are shown in FIG. 5 as relatively thin strips of material, may wider and/or longer than shown in FIG. 5 to suit a particular application.

As shown in FIG. 5, the cinching and sealing component 204 includes a first resilient elongate member 208A slidably disposed through a first fixation member 206A and a second fixation member 206B, a second resilient elongate member 208B slidably disposed through a third fixation member 206C and a fourth fixation member 206D, and a third resilient elongate member 208C slidably disposed through a fifth fixation member 206E and a sixth fixation member 206F. As described with respect to the embodiment of prosthesis 100 above, the cinching and sealing component 204 is configured to hold the prosthesis 200 in the radially compressed configuration for delivery to a desired treatment location. The cinching and sealing component 204, and more specifically, the first, second, and third resilient elongate members 208A, 208B, 208C are each further configured to provide a seal between the prosthesis 200 and the native anatomy when the prosthesis 200 is in the radially expanded configuration at the desired treatment location and the first, second, and third resilient elongate members 208A, 208B, 208C are each in a radially expanded state.

Referring again to FIG. 5, the first resilient elongate member 208A is configured to hold a first portion 211, or an inflow section 210 of the prosthesis 200 in the radially compressed configuration. The second resilient elongate member 208B is configured to hold a second portion 213, or an outflow section 212 of the prosthesis 200 in the radially compressed configuration. The third resilient elongate member 208C is configured to hold a third portion 214 in the radially compressed configuration. The third portion 214 is disposed between the first portion 211 and the second portion 213 of the prosthesis 200. In an embodiment, the third portion 214 may contain a prosthetic valve. Each resilient elongate member 208A-208C is disposed through the corresponding pair of fixation members such that each resilient elongate member encircles the prosthesis 200 in a generally circular path.

In embodiments hereof, each resilient elongate member (e.g. resilient elongate member 108, 208) may be tensioned by a tensioning mechanism configured to tension or relax/release the resilient elongate member as described below. In embodiments hereof, the tensioning mechanism may be a component of a delivery catheter configured to tension and relax/release the resilient elongate member.

Figure 6A:
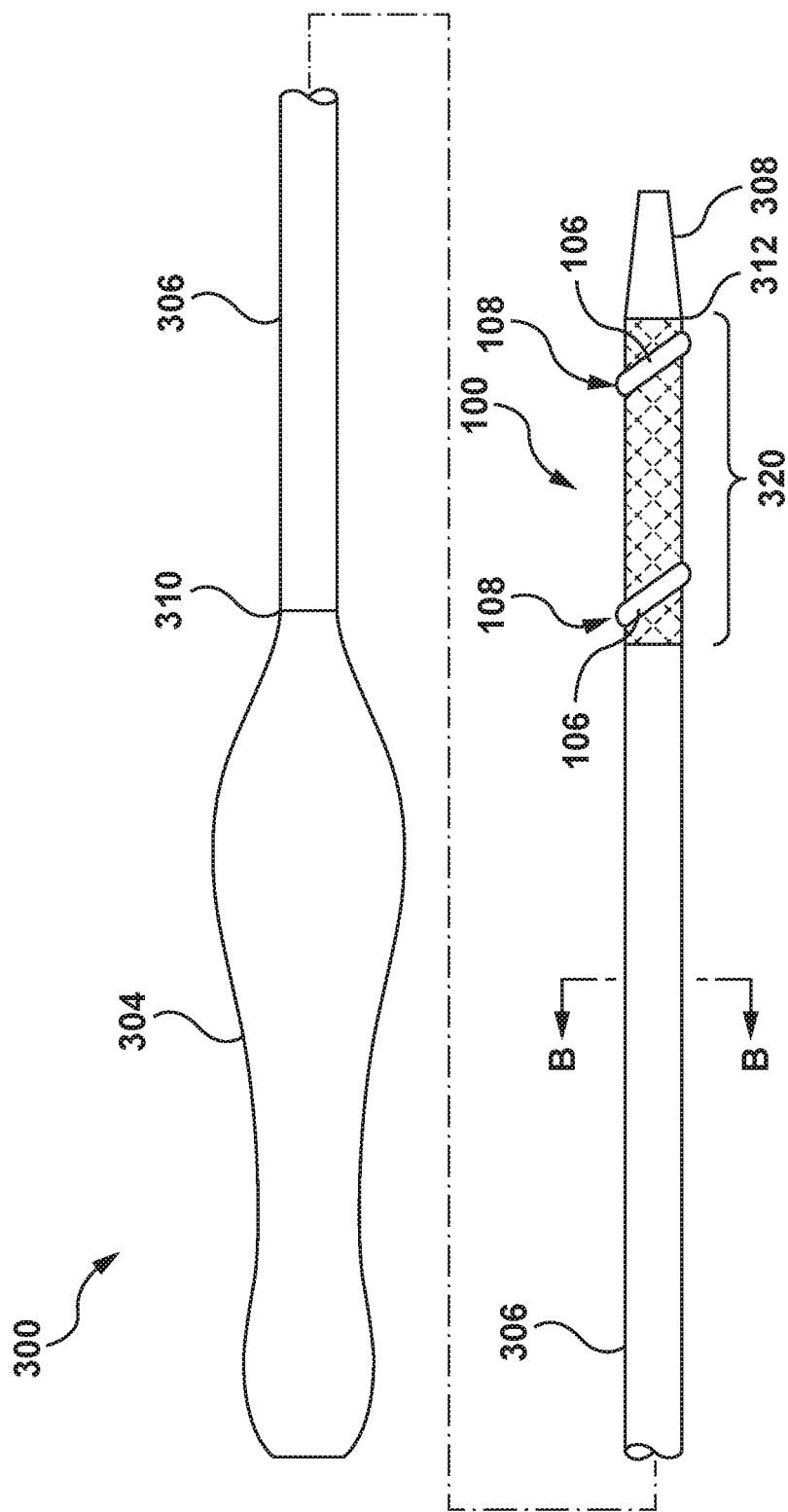
FIG. 6A depicts a side view of a delivery catheter configured to deliver the prosthesis of FIG. 1 according to embodiments hereof.
Figure 6B:
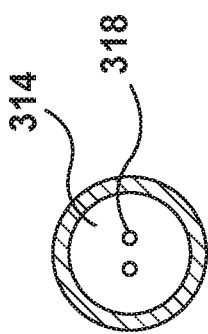
FIG. 6B depicts a cross-sectional view of the delivery catheter taken at line 6B-6B of FIG. 6A.
Figure 7:
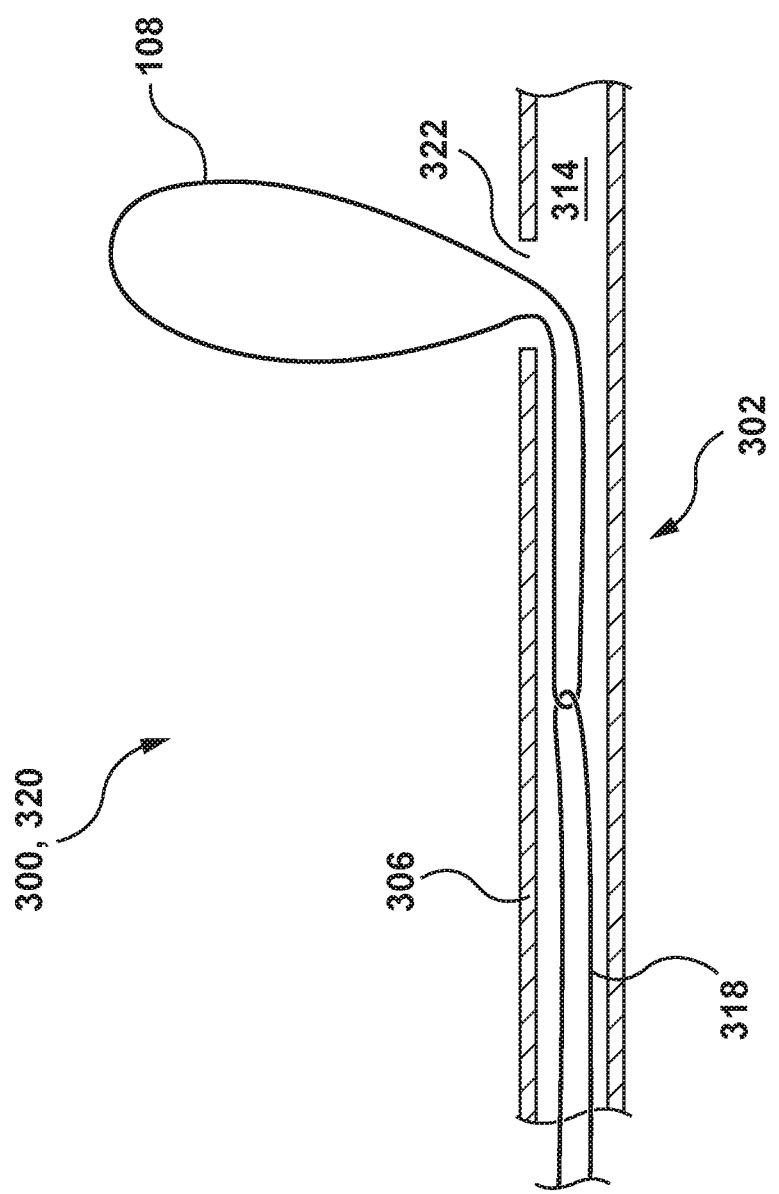
FIG. 7 depicts a sectional view of a distal portion of the delivery catheter of FIG. 6A with a tensioning mechanism and a resilient elongate member according to an embodiment hereof.

With reference to FIGS. 6A, 6B and 7, an exemplary delivery catheter 300 with a tensioning mechanism 302 (FIG. 7) suitable for use with the prosthesis 100 is shown. The delivery catheter 300 is shown in a delivery configuration in FIG. 6A with the prosthesis 100 loaded and held in the radially compressed configuration on a distal portion 320 thereof by a resilient elongate member 108. The delivery catheter 300 generally includes a handle 304, an elongate tubular shaft 306, and a distal tip 308. The elongate tubular shaft 306 includes a proximal end 310 and a distal end 312, and may be a multi-layer or multi-component structure as would be understood by one of ordinary skill in the art. The elongate tubular shaft further includes a lumen 314 extending from the proximal end 310 to the distal end 312, which is best shown in FIG. 6B. The lumen 314 is configured to slidably receive at least a tensioning mechanism 302. The distal tip 308 is coupled to the distal end 312 of the elongate tubular shaft 306. The lumen 314 of the elongate tubular shaft 306 may further be sized to slidably receive a guide-wire (not shown) such that the delivery catheter 300 may be advanced in an over-the-wire (OTW) configuration to the desired treatment location, or alternatively may include a separate lumen for receiving a guidewire. In some embodiments, the elongate tubular shaft 306 includes a plurality of lumens 314 for receiving one or more elongate members 108. The delivery catheter 300 may assume different forms, construction and features described, for example, and not by way of limitation, in U.S. Pat. No. 8,876,893 to Dwork, U.S. Pat. No. 7,662,186 to Bragga et al., U.S. Pat. No. 7,740,655 to Birdsall, and/or U.S. Pat. No. 8,579,963 to Tabor, each of which is incorporated by reference herein in their entirety.

The tensioning mechanism 302 is described herein with respect to the prosthesis 100, however it will be understood that embodiments of the tensioning mechanism 302 may be used with other prostheses. FIG. 7 depicts a resilient elongate member 108 partially extending within the lumen 314 and out of a port 322 in the elongate tubular shaft 306, and the tensioning mechanism 302 disposed within a portion of the lumen 314 of the elongate tubular shaft 306, with a remainder of the delivery catheter 300 and the prosthesis 100 removed for illustrative purposes only. In an embodiment, the tensioning mechanism 302 includes a tensioning member 318, e.g. suture, filament, wire, fiber, shaft, rod or cord that is releasably coupled to the resilient elongate member 108. The tensioning member 318 extends to a proximal end of the delivery catheter 300 and is longitudinally translatable to permit the resilient elongate member 108 to transition from the radially contracted state when in tension to the radially expanded state when relaxed. Within the lumen 314, the tensioning member 318 is threaded through the loop-shaped resilient elongate member 108 to be engaged with or coupled thereto. The tensioning member 318 is configured such that tension or pull force applied proximally to the tensioning member 318 correspondingly tensions or proximally pulls the resilient elongate member 108. Tension on the resilient elongate member 108 axially elongates the resilient elongate member 108, and transitions the member from the radially expanded state to the radially contracted state. Moreover, as the resilient elongate member 108 elongates and is drawn into the lumen 314 with the application of tension thereon, the resilient elongate member 108 applies a radially compressive force on the prosthesis 100 and the prosthesis 100 transitions to the radially compressed configuration. Thus, tension on the resilient elongate member 108 transitions the radially elongate member 108 from the radially expanded state to the radially contracted state and radially compresses and holds the prosthesis 100 in the radially compressed configuration. Release, slacking or relaxing of tension on the tensioning cord 318 correspondingly relaxes, slackens or releases the resilient elongate member 108, transitioning the resilient elongate member 108 to the radially expanded state and permitting the prosthesis 100 to controllably expand to the radially expanded configuration. As the prosthesis 100 radially expands and the resilient elongate member 108 axially elongates and transitions to the radially expanded state, the resilient elongate member 108 is drawn out of the lumen 314 via the port 322 to be disposed about the outer surface of the prosthesis 100. During or after the prosthesis 100 is returned to its radially expanded configuration, the resilient elongate member 108 may be decoupled from the tensioning member 318 of the tensioning mechanism 302.

While the prosthesis 100 is shown with one resilient elongate member 108, it will be understood that this is not meant to be limiting, and more than one resilient elongate member 108 may be utilized, as shown for example in the embodiment of FIG. 5. Accordingly as shown by example in FIG. 7A, two resilient elongate members 108A, 108B may be releasably coupled to a respective tensioning member 318A, 318B of a tensioning mechanism 302" to be coupled thereto within lumen 314, and to extend out of respective ports 322A, 322B in order to engage a prosthesis thereabout. Alternatively, more than one resilient elongate member 108 may be releasably coupled to the same tensioning member 318 and/or may extend though a single corresponding port 322 into the lumen 314.

Figure 8A:
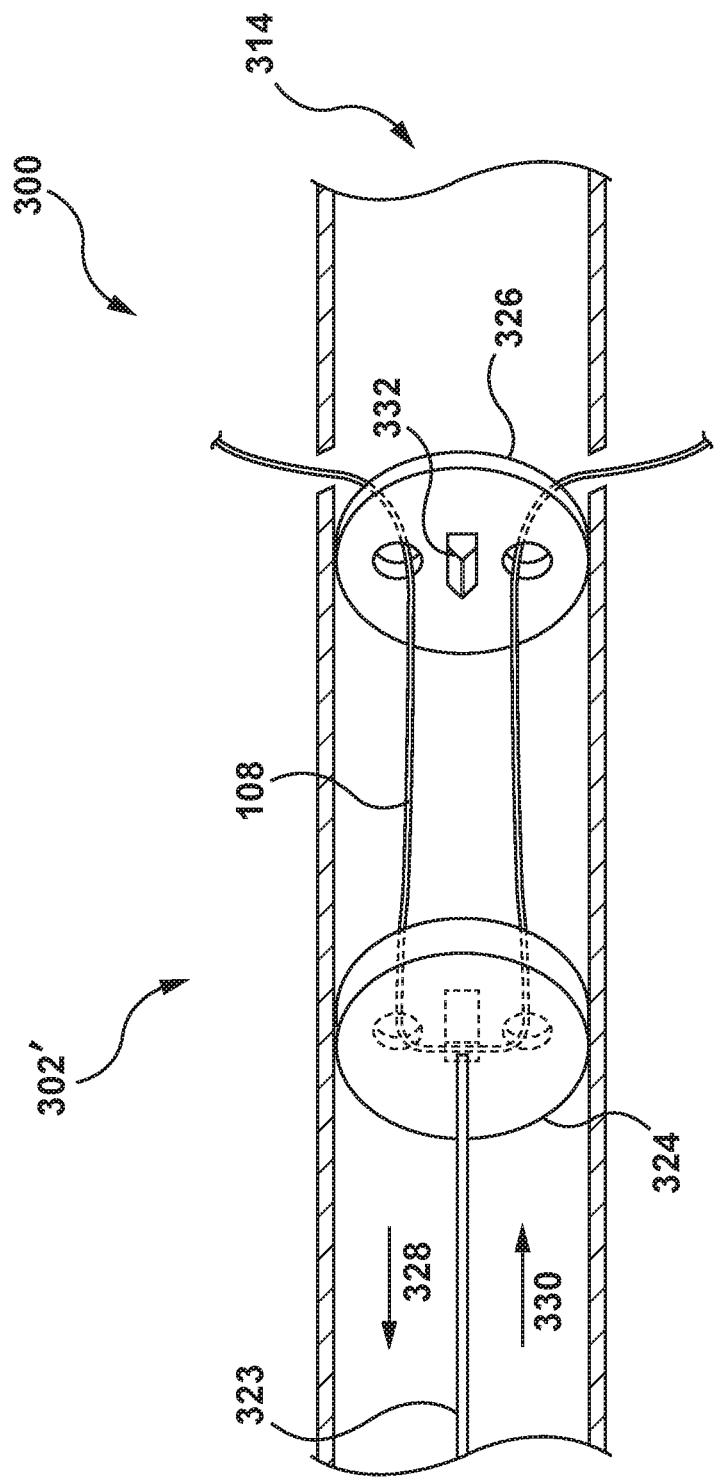
FIG. 8A depicts a perspective view of a tensioning mechanism and a resilient elongate member according to another embodiment hereof.
Figure 8B:
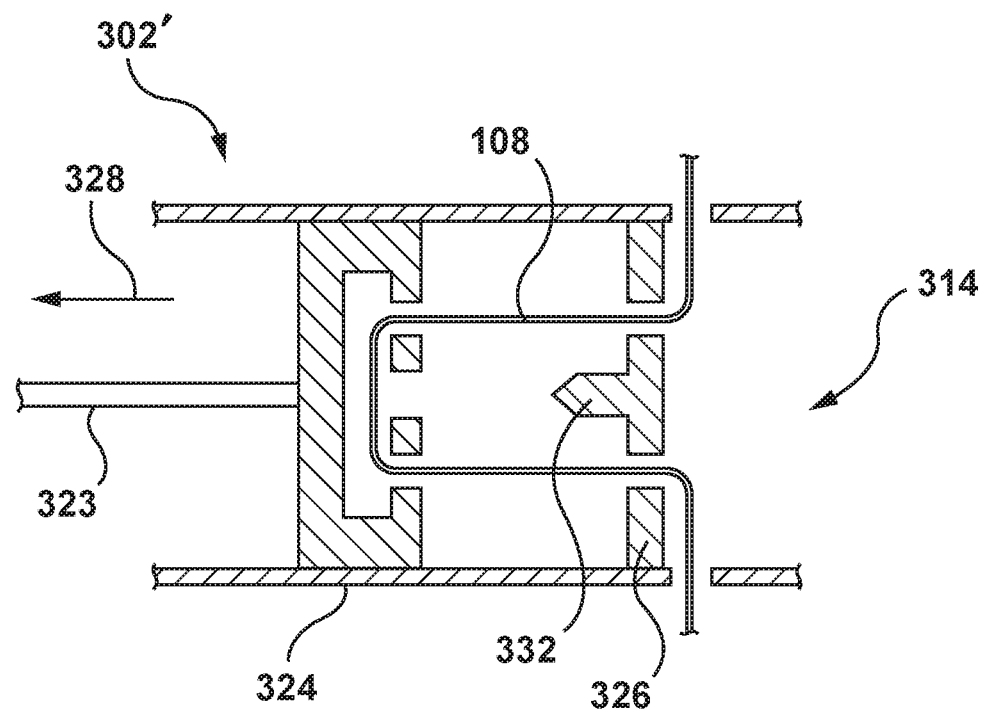
FIG. 8B depicts a sectional side view of the tensioning mechanism of FIG. 8A showing the resilient elongate member in tension.
Figure 8C:
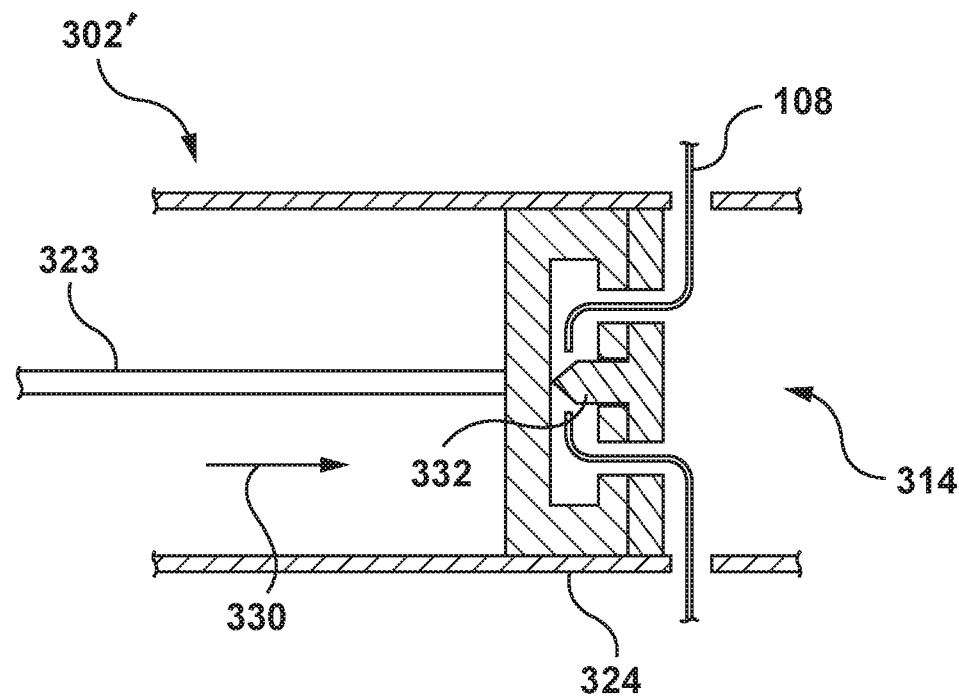
FIG. 8C depicts a sectional side view of the tensioning mechanism of FIG. 8A showing the resilient elongate member released.

In another embodiment, a tensioning mechanism 302' includes a first or tensioning plate 324 and a second or cutting plate 326, as shown in FIGS. 8A-8C. The tensioning mechanism 302' is disposed within and at a distal portion of the lumen 314 of the delivery catheter 300. The resilient elongate member 108 is threaded or routed through a pair of holes in each of the first and second plates 324, 326, as shown in FIG. 8A and in a side view in FIG. 8B. The first plate 324 is coupled to the proximal end of the delivery catheter 300 by a tensioning member 323, e.g., a rod or other suitable device such as a suture, filament, wire, fiber, shaft, or cord, such that the first plate 324 may be selectively longitudinally translated within the lumen 314 via the tensioning member 323. Accordingly, when the first plate 324 is pulled proximally in a direction of arrow 328, as shown in FIGS. 8A and 8B, the resilient elongate member 108 is correspondingly pulled in the direction of arrow 328, placing the resilient elongate member 108 in tension and transitioning the resilient elongate member 108 to the radially contracted state. Conversely, when the first plate 324 is pushed or allowed to translate distally in a direction of arrow 330, the resilient elongate member 108 is correspondingly relaxed, and tension is gradually reduced and eliminated, such that the resilient elongate member 108 is permitted to radially expand and axially shorten as it transitions to the radially expanded state. In one embodiment, the second plate 326 is fixed in place in the lumen 314. Eventually as the first plate 324 is translated distally to contact the second plate 326, the resilient elongate member 108 is caught between the first plate 324 and a cutter 332 of the second plate 326, wherein the cutter 332 severs or cuts the resilient elongate member 108, as shown in FIG. 8C. Once the resilient elongate member 108 is severed, the resilient elongate member 108 transitions to the radially expanded state and the prosthesis 100 transitions to the radially expanded state. The cutter 332 may be a blade, edge or other cutting device suitable for severing the resilient elongate member 108.

The interaction of the various components to deliver and deploy the prosthesis 100 at the desired treatment location are now described. Initially, the prosthesis 100 is loaded onto a distal portion 320 of the delivery catheter 300, as shown in FIG. 6A. The resilient elongate member 108 in the radially contracted state (in tension) holds the prosthesis 100 in the radially compressed configuration for delivery to the desired treatment site.

Once positioned at the desired treatment location, the tensioning mechanism 302 is operated to relax or release tension on the resilient elongate member 108. When relaxed, the resilient elongate member 108 transitions to the radially expanded state and permits the controlled expansion of the prosthesis 100 to the radially expanded configuration of FIG. 1. As the prosthesis 100 expands radially and the resilient elongate member 108 expands to the radially expanded state, the resilient elongate member 108 is drawn out of the lumen 314 of the delivery catheter 300 and is disposed about the outer surface of the frame 102 of the prosthesis 100. Further, as the resilient elongate member 108 transitions to the radially expanded state, the resilient elongate member 108 fills the channel 107 of the fixation member 106, extending the fixation member 106 outward to provide a seal between the prosthesis 100 and the native anatomy when the prosthesis 100 is in the radially expanded configuration, as shown in FIG. 4.

During deployment of the prosthesis 100 at the desired treatment location, the resilient elongate member 108 is uncoupled from the tensioning mechanism 302.

FIGS. 9, 10A, 10B and 11 depict a transcatheter prosthesis system 400 (hereafter referred to as the system 400) including a transcatheter prosthesis 402 (hereafter referred to as prosthesis 402 for simplicity), a plurality of elongate cinching members 404A, 404B and a delivery catheter 406 according to an embodiment hereof. The system 400 is configured to deliver, position and deploy the prosthesis 402 at a desired treatment location.

Figure 9:
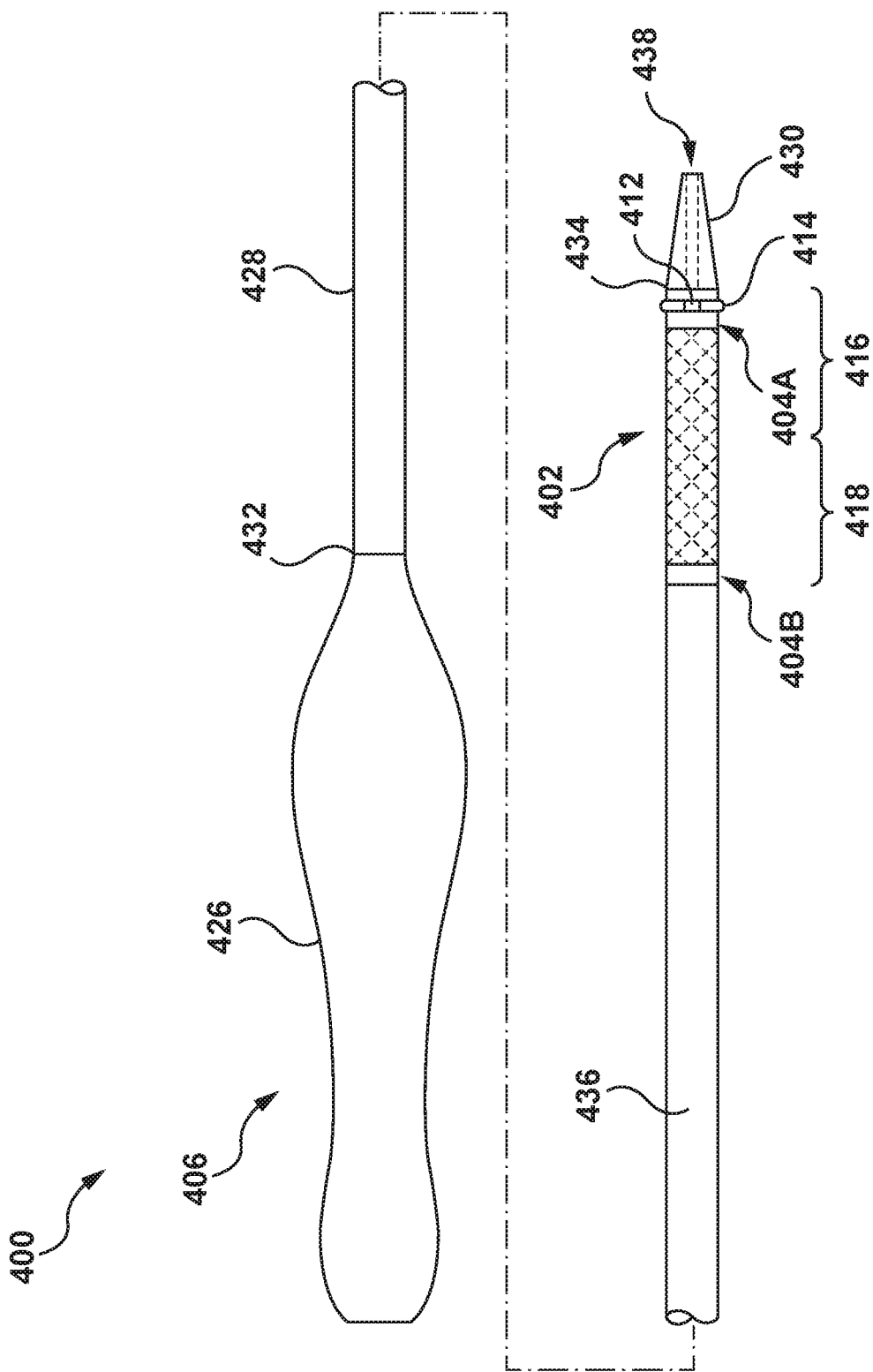
FIG. 9 depicts a transcatheter prosthesis system according to an embodiment hereof, wherein a prosthesis is in a radially compressed configuration.
Figure 10A:
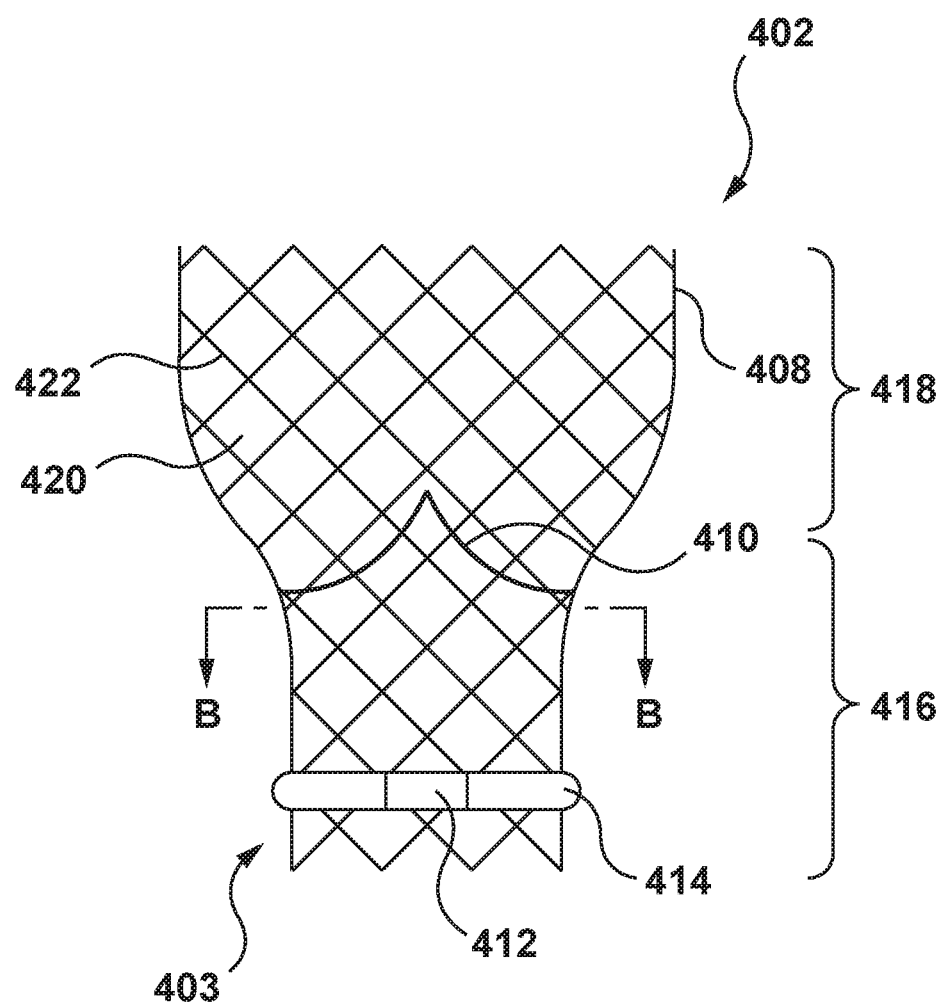
FIG. 10A depicts a side view of a prosthesis of the transcatheter prosthesis system of FIG. 9, wherein the prosthesis is in a radially expanded configuration.

The prosthesis 402 includes a frame or stent-like support structure 408, a valve component 410, as described earlier, coupled to and supported by the frame 408, an outer layer component (not shown), as described earlier, and a sealing component 403 configured to provide a seal between the prosthesis 402 and the native anatomy. The sealing component 403 includes a fixation member 412 configured to extend outwardly from an outer surface of the frame 408, and an elongate member 414 encircling at least a portion of the frame 408 according to an embodiment of the present invention, as shown in FIGS. 9 and 10A. The prosthesis 402 includes a radially compressed configuration for delivery and a radially expanded configuration of FIG. 10A when deployed at a desired treatment location.

In embodiments hereof, the frame 408 is self-expanding to return to a radially expanded configuration from a radially compressed configuration. The frame 408 includes an inflow section 416 and an outflow section 418, as shown in FIG. 10A. The frame 408 further includes a plurality of cells 420 formed by a plurality of struts 422. The cells 420 may have sizes that vary along the length of the frame 408.

Figure 10B:
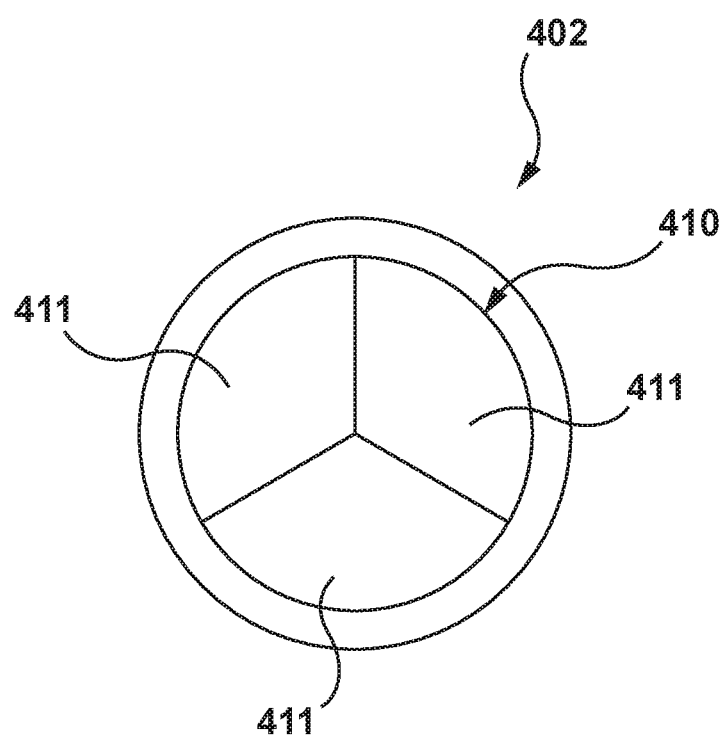
FIG. 10B depicts a top view of the prosthesis of FIG. 10A along line B-B thereof.

In embodiments hereof, the valve component 410 may comprise two, three, or four individual leaflets 411 assembled to simulate the leaflets of a native valve, as best shown in FIG. 10B. The components of the valve component 410 are formed of various materials, non-limiting examples of which include mammalian tissue such as porcine, equine or bovine pericardium, or a synthetic or polymeric material.

Referring back to FIG. 10A, in an embodiment, the fixation member 412 is a band of material or fabric configured to form a channel segment. The fixation member 412 is coupled to or formed from and configured to extend outwardly from the outer surface of the frame 408 or an outer layer, as described earlier, and is further configured with sufficient looseness to slidably receive the elongate member 414. The fixation member 412 may be constructed of materials, as described earlier, such as, but not limited to nickel-titanium alloys (e.g. NITINOL), nylon, polybutester, polypropylene, silk, polyester or other materials suitable for the purposes described herein. The fixation member 412 may be coupled to or formed from the frame 408 by a methods, as described earlier, such as, but not limited to fusing, welding, gluing, suturing or otherwise tied. Although the embodiment of FIG. 9 shows one (1) fixation member 412, this is not meant to be limiting, and more than one fixation member 412 may be utilized. Moreover, while shown and described herein as with a channel segment shape, the fixation member 412 may alternatively be formed, as described earlier, such as, but not limited to a loop, ring, band, or channel.

Figure 11:
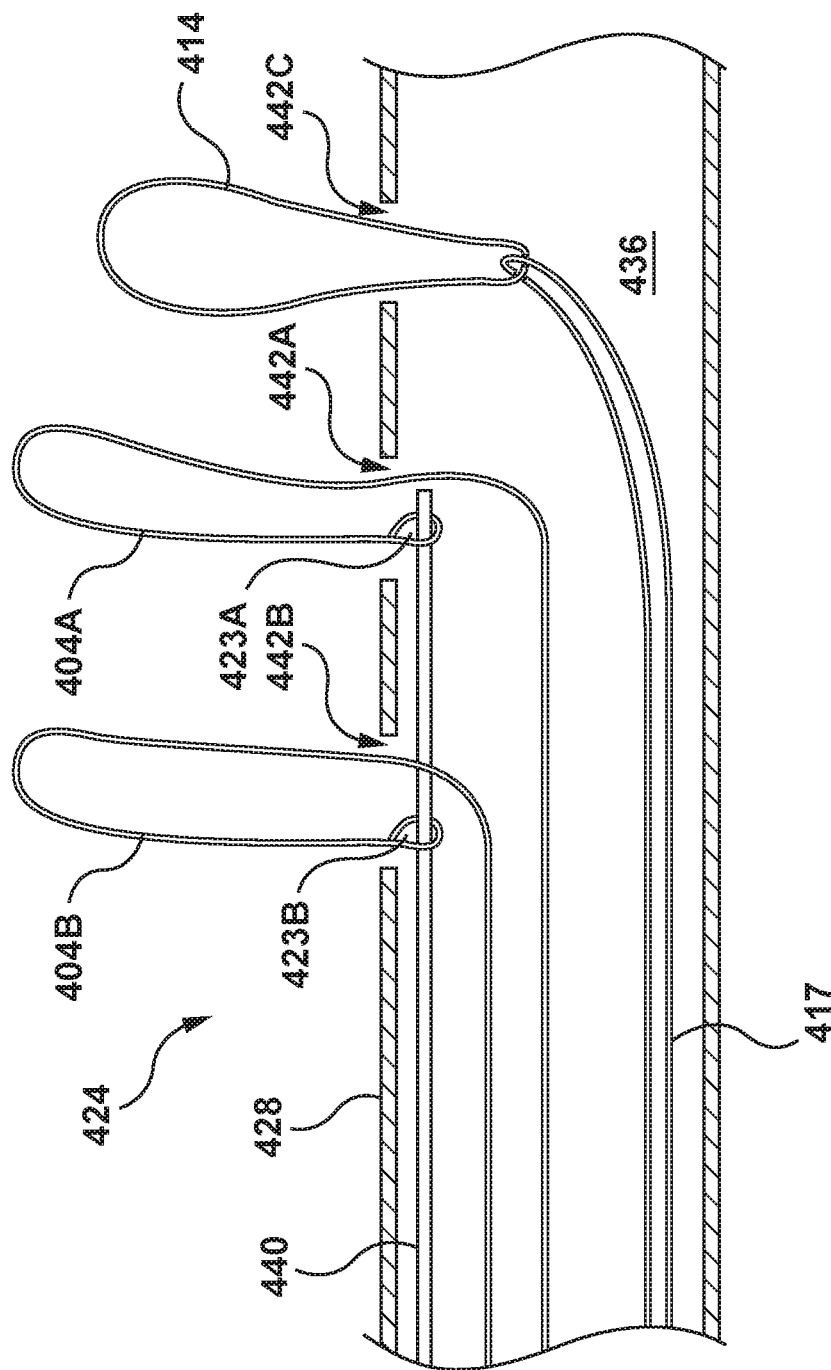
FIG. 11 depicts an enlarged sectional view a distal portion of the transcatheter prosthesis system of FIG. 9 with a cinching mechanism and an elongate member according to an embodiment hereof.

The elongate member 414 is sized to be long enough to encircle all or at least a portion of the outer surface of the frame 408 when the prosthesis 402 is in the radially expanded configuration, and is slidably disposed through the fixation member 412. In an embodiment, the elongate member 414 may be a resilient elongate member 414, as described in previous embodiments. In an embodiment, in contrast to a resilient elongate member described in the previous embodiments, the elongate member 414 may not be configured to have a radially contracted state when the elongate member 414 is in tension, and a radially expanded configuration when the elongate member 414 is relaxed. In an embodiment, the elongate member 414 may be an elongate cinching and sealing member used to cinch or hold the frame 408 of the prosthesis 402 in a radially compressed configuration for delivery to a desired treatment location and to create a seal between the prosthesis 402 and the native anatomy when the prosthesis 402 is in the radially expanded configuration at the desired treatment location. In an embodiment, the elongate member 414 is an elongate sealing member that is only used as a seal and not used to cinch or hold the frame 408 in a compressed configuration. The elongate member 414 is configured to slide along the fixation member 412 into a sealing position around the circumference of the prosthesis 402 as the prosthesis 402 is radially expanded during its deployment. When the prosthesis 402 is in the radially compressed configuration for delivery at least a portion of the elongate member 414 extends from an opening or access port 442C in the elongate tubular shaft 428 as shown in FIG. 11, and when the prosthesis 402 is in the radially expanded configuration to encircle at least a portion of the prosthesis 402 as shown in FIG. 10A. In an embodiment, the elongate member 414 may be described as having slack when the prosthesis 402 is in the radially compressed configuration, and in an embodiment may be partially held within the lumen 436, for example, by a releasable tension member 417, which may comprise a suture, fiber, filament, wire, shaft, rod, or cord. In an embodiment, the tension member 417 may provide just enough tension to remove slack from the elongate member 414 when the prosthesis 402 is in the radially compressed configuration for delivery. However, when the frame 408 of the prosthesis 402 transitions to the radially expanded configuration and the tension member 417 is withdrawn, the elongate member 414 may be pulled out of the lumen 436 into position, such as by sliding through the fixation member 412, to encircle a portion of the frame 408 in order to provide a seal between the prosthesis 402 and a native anatomy when the prosthesis 402 is in a radially expanded configuration. In an embodiment, the elongate member 414 may be tensioned using a tension mechanism including the tension member 417 to compress and hold a portion of the prosthesis 402 in the radially compressed configuration for delivery to the desired treatment location. The tension mechanism is configured to provide a desired amount of tension and/or relaxation/release for the elongate member 414. In one embodiment, the releasable tension mechanism may include a cutting mechanism, as describe earlier, to cut the elongate member 414 to thereby release the elongate member 414 from the tension member 417. Cutting the elongate member 414 to release it from the tension member 417 may be desired if the elongate member 414 is configured to only seal a portion of the circumference of the prosthesis 402. In an alternative embodiment, it may be desirable not to cut the elongate member 414 if the elongate member 414 is configured to form a complete seal around the entire circumference of the prosthesis 402.

In an embodiment, the elongate member 414 may be a resilient elongate member, as described above with reference resilient elongate member 108, having a radially contracted state when in tension and a radially expanded state when relaxed, wherein that the resilient elongate member provides a seal between the prosthesis 402 and the native anatomy when the prosthesis is in the radially expanded configuration and the resilient elongate member is in the radially expanded state, and wherein when the elongate resilient member is in the radially contracted state is configured to cinch or hold at least a portion of the prosthesis 402 in a radially compressed configuration for delivery.

Although FIG. 9 shows one (1) elongate member 414 passing through one (1) fixation member 412 and encircling the inflow section 416 of the frame 408 in a generally circular path, this is not meant to be limiting, and more than one (1) elongate member 414 may be utilized, passing through more or fewer fixation members 412 at other locations of the prosthesis 402 and in other paths about the frame 408. The elongate member 414 may be formed, as previously described, of one or more biocompatible materials such as, but not limited to metals, e.g. stainless steel, nickel-titanium alloys (e.g. NITINOL), polymers, e.g.

nylon, polybutester, polypropylene, silk, polyester or other materials suitable for the purposes described herein.

Each elongate cinching member 404A, 404B of the transcatheter system 400 may be a suture, fiber, filament, wire, or cord configured to hold a portion of the prosthesis 402 in the radially compressed configuration for delivery to the desired treatment location. Each elongate cinching member 404A, 404B includes a first end (not shown) extending to a proximal end of a delivery catheter 406 and a second end 423A, 423B, shown in FIG. 12 and described below. Each elongate cinching member 404A, 404B is releasable to permit the corresponding portion of the prosthesis 402 held in the radially compressed configuration to return to the deployed or radially expanded configuration.

More particularly, as shown in FIG. 9, each elongate cinching member 404A, 404B encircles the prosthesis 402 such that pulling or tensioning the elongate cinching member 404A, 404B radially compresses the prosthesis 402, and releasing/relaxing each elongate cinching member 404A, 404B controls the expansion and deployment of the corresponding portion of the prosthesis 402. Each elongate cinching member 404A, 404B encircles or extends circumferentially in a generally circular path about the outer surface of the frame 408 of the prosthesis 402. Each elongate cinching member 404A, 404B may be formed of one or more biocompatible materials such as, but not limited to metals, e.g. stainless steel, nickel-titanium alloys (e.g. NITINOL), polymers, e.g. nylon, polybutester, polypropylene, silk, polyester or other materials suitable for the purposes described herein. Further details and examples of suitable elongate cinching materials and configurations for retaining self-expanding transcatheter prostheses are described in U.S. Patent Publication No. 2014/0330368 to Gloss, which is incorporated by reference herein in its entirety.

In embodiments hereof, the plurality of elongate cinching members 404A, 404B may be tensioned by a cinching mechanism 424 configured to tension or relax/release the plurality of elongate cinching members 404A, 404B such that the plurality of elongate cinching members 404A, 404B radially compress or permit radial expansion of the prosthesis 402. In embodiments hereof, the cinching mechanism 424 is a component of the delivery catheter 406. However, this is not meant to be limiting, and other configurations of cinching mechanisms not formed as a component of a delivery catheter are possible.

The delivery catheter 406 is shown in a delivery configuration in FIG. 9 with the prosthesis 402 loaded and held in the radially compressed configuration by a first and second elongate cinching member 404A, 404B and, in some embodiments, by the elongate member 414. The delivery catheter 406 includes a handle 426, an elongate tubular shaft 428, and a distal tip 430. The elongate tubular shaft 428 includes a proximal end 432, a distal end 434, and a lumen 436 extending from the proximal end 432 to a distal portion of the elongate tubular shaft 428. The lumen 436 is configured to slidably receive the cinching mechanism 424, examples of which are described below and shown in FIGS. 11 and 12, and the elongate member 414. The distal tip 430 is coupled to the distal end 434 of the elongate tubular shaft 428. The elongate tubular shaft 428 may further include a guidewire lumen 438 extending from the proximal end 432 to the distal end of the distal tip 430, sized to slidably receive a guidewire (not shown) such that the delivery catheter 406 may be advanced in an over-the-wire (OTW) configuration to the desired treatment location. The delivery catheter 406 may assume different forms, construction and features described, for example, and not by way of limitation, in U.S. Pat. No. 8,876,893 to Dwork, U.S. Pat. No. 7,662,186 to Bragga et al., U.S. Pat. No. 7,740,655 to Birdsall, U.S. Pat. No. 8,579,963 to Tabor, and/or U.S. Patent Publication No. 2014/0330368 to Gloss, each of which was previously incorporated by reference herein in its entirety.

The prosthesis 402 is disposed along a distal segment of the elongate tubular shaft 428, as shown in FIG. 9. The first elongate cinching member 404A encircles, or surrounds the inflow section 416 of the prosthesis 402 and is configured to hold the inflow section 416 in the radially compressed configuration for delivery to the desired treatment location. The second elongate cinching member 404B encircles, or surrounds the outflow section 418 of the prosthesis 402 and is configured to hold the outflow section 418 in the radially compressed configuration for delivery to the desired treatment location. Thus, the first and second elongate cinching members 404A, 404B compressively hold at least a portion of the prosthesis 402 in the radially compressed configuration for delivery to the desired treatment location. In some embodiments, the elongate member 414 is an elongate cinching and sealing member that also compressively holds at least a portion of the prosthesis 402 in the radially compressed configuration for delivery to the desired treatment location. In other embodiments, the elongate member 414 may be only used as an elongate sealing member and does not hold any portion of the prosthesis 402 in the radially compressed configuration.

FIG. 11 is an enlarged sectional view of a distal portion of the elongate tubular shaft 428 removed from the remainder of the delivery catheter 406 for clarity. FIG. 11 illustrates the cinching mechanism 424 according to an embodiment hereof. The cinching mechanism 424 includes the first and second elongate cinching members 404A, 404B, and a release pin 440. A portion of the cinching mechanism 424 is slidably disposed within the lumen 436 and is configured to radially compress at least a portion of the prosthesis 402 to the radially compressed configuration of FIG. 9 for delivery to a desired treatment location. The cinching mechanism 424 is further configured to permit the release or deployment of the prosthesis 402 from the radially compressed configuration to the radially expanded configuration at the desired treatment location. As best shown in FIG. 11, each elongate cinching member 404A, 404B extends distally from the proximal end of the delivery catheter 406, through the lumen 436, exiting the lumen 436 though a respective opening or port 442A, 442B in the elongate tubular shaft 428, encircles the prosthesis 402 (not shown in FIG. 11 for clarity), and extends back through the respective opening or port 442A, 442B into the lumen 436, where the second end 423A, 423B of the elongate cinching member 404A, 404B is releasably coupled to the release pin 440, as shown in FIG. 11. The release pin 440 is operably coupled to the proximal end of the delivery catheter 406. The cinching mechanism 424 is further configured such that remote actuation of the release pin 440 (e.g. via an actuator such as a knob, or lever of the delivery catheter 406) with the prosthesis 402 in the radially compressed configuration releases the elongate cinching member 404A, 404B, thereby permitting the prosthesis 402 to expand to the radially expanded configuration. Once the prosthesis 402 is in the radially expanded configuration, each elongate cinching member 404A, 404B may be retracted proximally to remove the respective elongate cinching member 404A, 404B from its position about the prosthesis 402.

Figure 12:
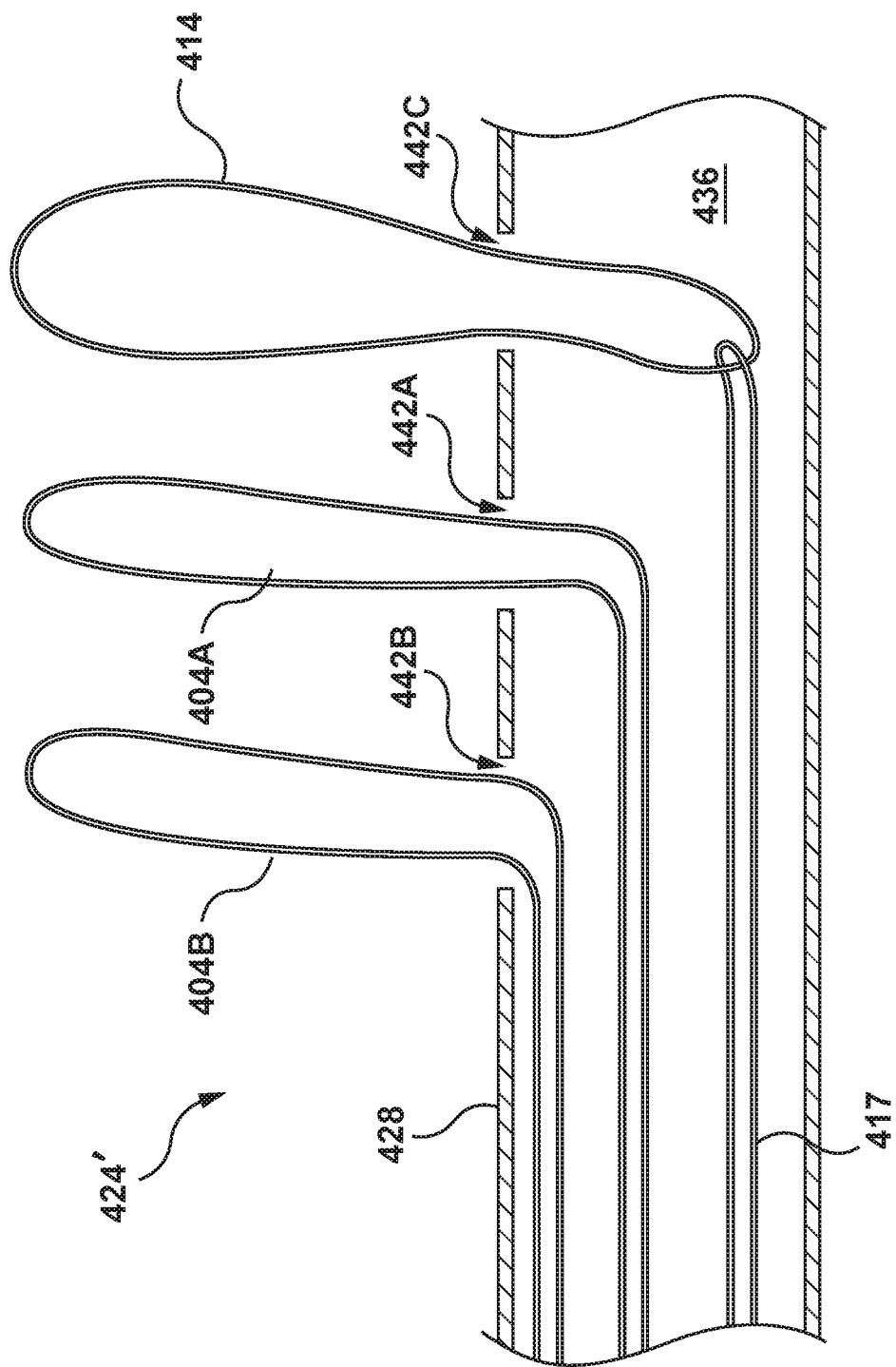
FIG. 12 depicts an enlarged sectional view of a distal portion of the transcatheter prosthesis system of FIG. 9 with a cinching mechanism and an elongate member according to another embodiment hereof.

FIG. 12 shows a cinching mechanism 424' with the elongate member 414 of the prior embodiments according to another embodiment hereof. In the embodiment of FIG. 12, each elongate cinching member 404A, 404B extends distally from the proximal end of the delivery catheter 406, through the lumen 436, exiting the lumen 436 though a respective opening or port 442A, 442B in the elongate tubular shaft 428, encircles the prosthesis 402 (not shown in FIG. 12 for clarity), and extends back through the respective opening or port 442A, 442B and proximally within the lumen 436 to the proximal end of the delivery catheter 406. Each cinching member 404A, 404B is configured to be releasably held in tension at a proximal end of the delivery catheter 406 such that the prosthesis 402 is held in the radially compressed configuration for delivery to a desired treatment location. Each cinching member 404A, 404B is further configured to be releasable to permit the corresponding portion of the prosthesis 402 to controllably expand to the radially expanded configuration. Once the prosthesis 402 is in the radially expanded configuration, a first end of each elongate cinching member 404A, 404B may be released and a corresponding second end of each elongated cinching member 404A, 404B retracted proximally to remove the respective elongate cinching member 404A, 404B from its position about the prosthesis 402.

With an understanding of the components of the transcatheter prosthesis system 400, it is now possible to describe the interaction of the various components to deliver, position and deploy the prosthesis 402 the desired treatment location. The prosthesis 402 is loaded onto the delivery catheter 406, as shown in FIG. 9. The first and second elongate cinching members 404A, 404B combine to hold at least a portion of the prosthesis 402 in the radially compressed configuration for delivery to the desired treatment site, and the elongate member 414, which can be a resilient elongate member, an elongate cinching and sealing member, or an elongate sealing member, is threaded through the fixation member 412 and coupled to a tension member 417 with the lumen 436 of the delivery catheter 406.

The transcatheter prosthesis system 400 is advanced through a vasculature. Once the prosthesis 402 is positioned at the desired treatment location, the cinching mechanism 424 and cord 417 are released and the prosthesis 400 expands to the radially expanded configuration. The elongate member 414 being in a slackened state during delivery is pulled free of the lumen 436 through the opening or port 442C by the expanding frame 408 to encircle the frame 408 when the prosthesis 400 expands to the radially expanded configuration, as shown in FIG. 10A. At all times, the elongate member 414 is slidably coupled through the fixation member 412. Accordingly, the elongate member 414 provides a seal between the prosthesis 402 and the native anatomy when the prosthesis 402 is in the radially expanded configuration shown in FIG. 10A.

With the prosthesis 402 is deployed and sealed at the desired treatment location, the elongate cinching members 404A, 404B may be removed from their positions around the prosthesis 402.

While the cinching mechanism 424 has been described with two (2) elongate cinching members 404A, 404B, it will be understood that more or fewer elongate cinching members 404A, 404B may be utilized. Additional details and examples of suitable cinching mechanisms for retaining self-expanding transcatheter prostheses are described in U.S. Patent Publication No. 2014/0330368 to Gloss, previously incorporated herein by reference in its entirety. While the sealing component 403 has been described with a fixation member 412 and an elongate member 414, it will be understood that one or more fixation members 412 and/or more elongate members 414 may be utilized. While the elongate member 414 has been described as being distal of the elongate cinching members 404A, 404B, it will be understood that one or more elongate members 414 can be positioned proximal of one or more elongate cinching members 404A, 404B.

Figure 13:
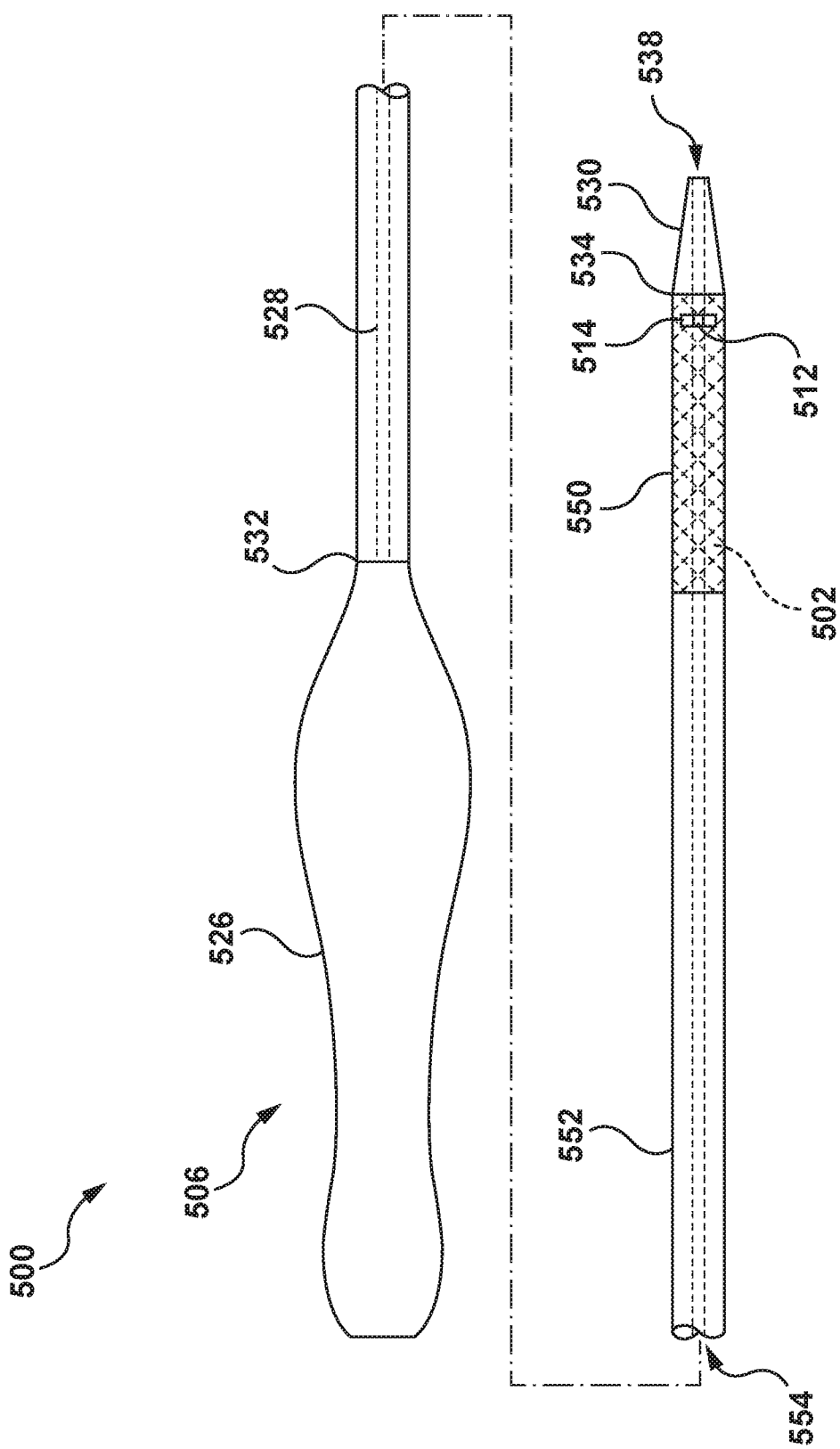
FIG. 13 depicts a transcatheter prosthesis system according to another embodiment hereof, wherein a prosthesis is in a radially compressed configuration within a delivery catheter.

FIG. 13 shows a transcatheter prosthesis system 500 including a transcatheter prosthesis 502 (hereafter referred to as prosthesis 502) and a delivery catheter 506 according to another embodiment hereof. The prosthesis 502 includes a fixation member 512 and an elongate sealing member 514 that is coupled to a releasable tension member, which may comprise a suture, fiber, filament, wire, shaft, rod, or cord, within a lumen of the delivery catheter 506, as similarly described in the embodiments of FIGS. 9-12. The prosthesis 502, the fixation member 512 and the elongate sealing member 514 are similar to the prosthesis 402, the fixation member 412 and the elongate member 414, when used solely as an elongate sealing member, as described previously. Therefore, construction and alternatives of the prosthesis 502, the fixation member 512 and the elongate sealing member 514 will not be repeated. In the embodiment of the transcatheter prosthesis system 500, the prosthesis 502 is held in the radially compressed configuration by a distal portion 550, such as a capsule or distal portion of an outer sheath, of the delivery catheter 506.

As shown in FIG. 13, the delivery catheter 506, suitable for delivering and deploying the prosthesis 502 with the prosthesis 502 in the radially compressed configuration within the distal portion 550 of an outer sheath 552. In an embodiment, the distal portion 550 may be referred to as a capsule and may be constructed as described in U.S. Pat. No. 8,926,692 to Dwork, U.S. Pat. No. 8,998,980 to Shipley et al., U.S. Pat. No. 8,512,401 to Murray, III et al., and/or U.S. Pat. No. 8,852,271 to Murray, III et al., each of which is incorporated by reference in its entirety. The delivery catheter 506 includes a handle 526, an elongate tubular shaft 528, a distal tip 530 and the outer sheath 552. The elongate tubular shaft 528 includes a proximal end 532, a distal end 534 guidewire lumen 538. The guidewire lumen 538 extends the length of the catheter 506 and is sized to slidably receive a guidewire (not shown in FIG. 13).

The outer sheath 552 includes the distal portion 550, which forms a distalmost portion or segment thereof. The outer sheath 550 includes a lumen 554 extending from a proximal end to a distal end thereof. The elongate tubular shaft 528 extends within the lumen 554. The distal portion 550 is configured to hold the prosthesis 502 in the radially compressed configuration for delivery. The outer sheath 552 is proximally retractable relative to the elongate tubular shaft 528 to release and deploy the prosthesis 502 from the distal portion 550. More precisely, the outer sheath 552 is coupled to a retraction mechanism of the delivery catheter 506. Various retraction mechanisms may be utilized, such as, but not limited to an axially-slidable lever, a rotatable rack and pinion gear, or other mechanisms suitable for the purposes described herein.

Accordingly, and as shown in FIG. 13, the prosthesis 502 is loaded onto the delivery catheter 506 with the distal portion 550 holding the prosthesis 502 in the radially compressed configuration and the elongate sealing member 514 disposed about the outer surface of the frame 508 of the prosthesis 502 and extending within the lumen of the elongate tubular shaft 528 for delivery. Once the prosthesis 502 is positioned at the desired treatment location, the distal portion 550 is retracted proximally, and the elongate sealing member 514 is drawn out of a lumen of the delivery catheter 506 via an opening or port (not shown) during expansion of the prosthesis 502 to the radially expanded configuration. In one embodiment, a tension member comprising a fiber, filament, wire, shaft, rod, or cord (not shown) releases the elongate sealing member 514, to permit the elongate sealing member 514 to be drawn out of the lumen of the delivery catheter 506 during expansion of the prosthesis 502 to the radially expanded configuration. As the prosthesis 502 expands radially, the elongate sealing member 514, which is slidable relative to the fixation member 512, gradually encircles the outer surface of the prosthesis to provide a seal between the prosthesis 502 and the native anatomy.

Figure 14:
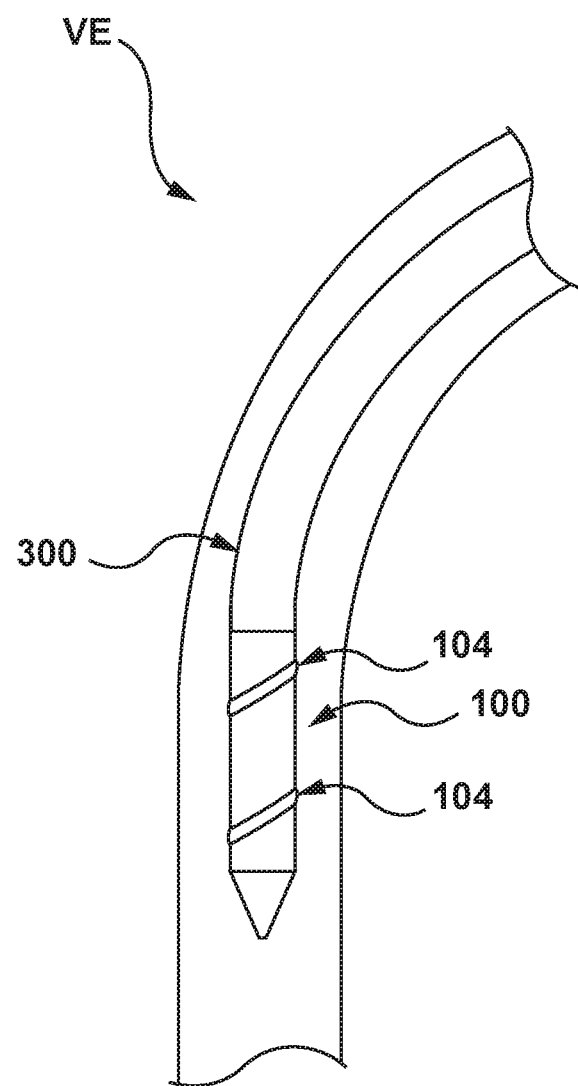
FIG. 14 is an illustration of the prosthesis of FIG. 1 in situ, wherein the prosthesis is shown in a radially compressed configuration within a delivery catheter that is positioned within a vessel of the native anatomy.
Figure 15:
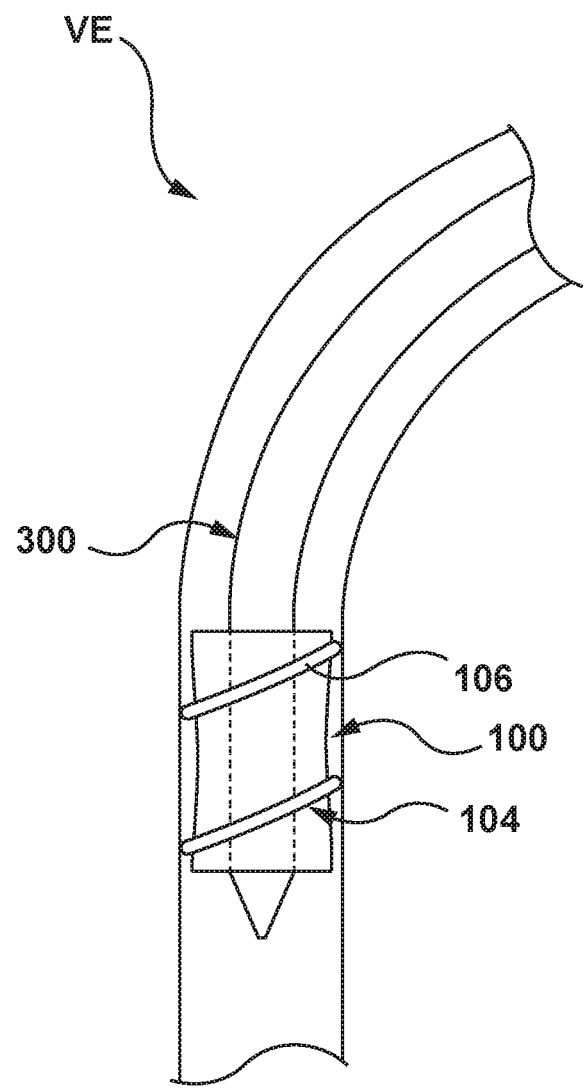
FIG. 15 is an illustration of the prosthesis of FIG. 1 in situ, wherein the prosthesis is shown in a radially expanded configuration released from a delivery catheter, and deployed such that a resilient elongate member is providing a seal between the prosthesis and the vessel.

FIGS. 14 and 15 are sectional cut-away views of a vessel VE illustrating a method of delivering, deploying and sealing the prosthesis 100 of FIG. 1 in accordance with an embodiment hereof. With reference to FIGS. 6A and 14, a distal segment of a delivery catheter 300 is shown positioned at the vessel VE, with the prosthesis 100 loaded thereon and held in the radially compressed configuration by the cinching and sealing component 104. Intravascular access to the vessel VE or valve may be achieved via a percutaneous entry point in an artery or vein, e.g. femoral, brachial, radial, or auxiliary artery, a.k.a. the Seldinger technique, extending through the vasculature to the desired treatment location. Alternatively, access to a native heart valve may be achieved via a percutaneous entry point in a heart wall. As will be understood, a handle (not shown in FIGS. 14 and 15), as well as a length of a proximal section (not shown in FIGS. 14 and 15) of the delivery catheter 300 are exposed external of the patient for access and manipulation by a clinician, even as the prosthesis 100 is positioned at the desired treatment location. Although not shown in FIG. 14, optionally, a guidewire and/or a guide catheter may be utilized with the delivery catheter 300, with the delivery catheter 300 slidably advanced over the guidewire and/or within the guide catheter.

Once the prosthesis 100 in the radially compressed configuration is positioned at the desired treatment location, and in a next delivery step, the delivery catheter 300 is manipulated to release or relax tension on the resilient elongate cinching and sealing member 108, obscured by view by the fixation member 106, thereby permitting the controlled expansion of the prosthesis 100 from the radially collapsed configuration of FIG. 14 to the radially expanded configuration of FIG. 15. Additionally, once tension is released from the resilient elongate member 108, the resilient elongate member 108 transitions to the radially expanded state, filling and expanding the fixation member 106 outward such that the resilient elongate member 108 and the fixation member 106 of the cinching and sealing component 104 provides a seal preventing blood flow between the prosthesis 100 and the native anatomy of the vessel VE or valve annulus and/or leaflets.

During deployment or following full deployment of the prosthesis 100, the resilient elongate member 108 is uncoupled from the tensioning mechanism 302.

Following the delivery, placement and deployment of the prosthesis 100 at the desired location, the delivery catheter 300 and remaining guidewire and/or guide catheter (if any) may be removed using established transcatheter procedures.

Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's delivery and positioning of the prosthesis 100 at the target region.

While the method of FIGS. 14 and 15 illustrate the prosthesis 100 deployed within a vessel VE, this is not meant to be limiting, and the method in combination with other transcatheter prostheses (e.g. a transcatheter valve prosthesis) may be utilized at other locations such as, but not limited to a heart valve, e.g. aortic, mitral, pulmonic, or tricuspid, and an aortic aneurysm.

The valve prostheses 100, 200, 402, and 502 are illustrated herein to facilitate description of the devices and methods according to embodiments hereof. It is understood that any number of alternate valve prostheses can be used with the devices and methods described herein. Moreover, each prosthesis may incorporate or exclude a valve component based upon the specific application.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A system for delivering a transcatheter prosthesis comprising:
   a prosthesis having a radially compressed configuration for delivery within a vasculature and a radially expanded configuration for deployment within a native anatomy comprising,
      a frame, and
      an elongate member encircling at least a first portion of the frame, wherein the elongate member is attached to the frame by at least one fixation member,
   wherein a cross-section of the elongate member has an expanded outer diameter in a radially expanded state and a contracted outer diameter in a radially contracted state, the contracted outer diameter of the cross-section of the elongate member being less than the expanded outer diameter of the cross-section of the elongate member, and
   wherein the elongate member in the radially expanded state provides a seal between the prosthesis and the native anatomy when the prosthesis is in the radially expanded configuration; and
   a delivery catheter including an elongate cinching member encircling at least a second portion of the frame of the prosthesis, wherein the elongate cinching member is configured to hold at least the second portion of the frame of the prosthesis in the radially compressed configuration.

2. The system of claim 1, wherein the at least one fixation member extends outwardly from an outer surface of the frame and the elongate member is slidable relative to the fixation member.

3. The system of claim 2, wherein the elongate member is a resilient elongate member, the resilient elongate member having the radially contracted state when in tension and the radially expanded state when relaxed.

4. The system of claim 3, wherein the resilient elongate member in the radially expanded state fills the at least one fixation member to extend the at least one fixation member outwardly, whereby the resilient elongate member and the at least one fixation member provide the seal between the prosthesis and the native anatomy when the prosthesis is in the radially expanded configuration.

5. The system of claim 4, wherein the at least one fixation member comprises a plurality of fixation members spaced apart about a circumference of the frame, and the resilient elongate member is slidably disposed within the plurality of fixation members.

6. The system of claim 3, wherein the resilient elongate member in the radially contracted state is configured to cinch or hold the first portion of the frame of the prosthesis in the radially compressed configuration for delivery.

7. The system of claim 1, wherein the elongate member has a generally circular path about the frame.

8. A transcatheter prosthesis having a radially compressed configuration for delivery within a vasculature and a radially expanded configuration for deployment within a native anatomy, the prosthesis comprising:
   a frame having a radially compressed configuration for delivery within a vasculature and a radially expanded configuration for deployment within a native anatomy;
   a fixation member extending outwardly from an outer surface of the frame; and
   an elongate member encircling at least a portion of the frame,
   wherein a cross-section of the elongate member has an expanded outer diameter in a radially expanded state and a contracted outer diameter in a radially contracted state, the contracted outer diameter of the cross-section of the elongate member being less than the expanded outer diameter of the cross-section of the elongate member,
   wherein the elongate member is slidably disposed within the fixation member, and
   wherein the elongate member in the radially expanded state provides a seal between the prosthesis and the native anatomy when the prosthesis is in the radially expanded configuration.

9. The transcatheter prosthesis of claim 8, wherein the elongate member is a resilient elongate member having the radially contracted state when in tension and the radially expanded state when relaxed.

10. The transcatheter prosthesis of claim 9, wherein the resilient elongate member and the fixation member provide the seal between the prosthesis and the native anatomy when the prosthesis is in the radially expanded configuration and the resilient elongate member is in the radially expanded state.

11. The transcatheter prosthesis of claim 8, wherein the elongate member has a generally circular path about the outer surface of the frame.

12. The transcatheter prosthesis of claim 8, wherein the fixation member comprises a plurality of fixation members spaced apart about a circumference of the frame, and the elongate member is disposed within the plurality of fixation members.

13. The transcatheter prosthesis of claim 8, wherein the prosthesis is a valve prosthesis, and the frame of the prosthesis includes a prosthetic valve component disposed within and secured to the frame.

14. A method of deploying and sealing a prosthesis within a native anatomy comprising:
   loading a prosthesis with an elongate member onto a delivery catheter, wherein a cross-section of the elongate member has an expanded outer diameter in a radially expanded state and a contracted outer diameter in a radially contracted state, the contracted outer diameter of the cross-section of the elongate member being less than the expanded outer diameter of the cross-section of the elongate member, and wherein the elongate member encircles at least a portion of a frame of the prosthesis and provides a seal between the prosthesis and the native anatomy when the prosthesis is in a radially expanded configuration, and
   wherein the elongate member is configured to axially elongate under tension to transition the elongate member from the radially expanded state to the radially contracted state; and
   deploying the prosthesis in the radially expanded configuration at the native anatomy, wherein the elongate member seals between the prosthesis and the native anatomy to prevent blood flow therebetween.

15. The method of claim 14, wherein the elongate member is a resilient elongate member configured to hold the prosthesis in the radially compressed configuration and the step of deploying the prosthesis includes releasing the resilient elongate member to permit the prosthesis to return to the radially expanded configuration.

16. The method of claim 14, wherein the delivery catheter comprises an elongate cinching member configured to aid in holding at least a portion of the prosthesis in the radially compressed configuration, and wherein the step of deploying the prosthesis includes releasing and removing the elongate cinching member of the delivery catheter to permit the prosthesis to return to the radially expanded configuration.

17. The method of claim 16, wherein the elongate member is a resilient elongate member configured to hold at least a portion of the prosthesis in the radially compressed configuration and the step of deploying the prosthesis further includes releasing the resilient elongate member to permit the prosthesis to return to the radially expanded configuration.

18. The method of claim 17, wherein the resilient elongate member is configured to hold a first portion of the prosthesis in the radially compressed configuration and the elongate cinching member is configured to hold a second portion of the prosthesis in the radially compressed configuration, and
   wherein releasing the resilient elongate member permits the first portion of the prosthesis to return to the radially expanded configuration, and
   wherein releasing and removing the elongate cinching member of the delivery catheter permits the second portion of the prosthesis to return to the radially expanded configuration.

19. The method of claim 18, wherein the prosthesis is a valve prosthesis and the native anatomy is a native heart valve.

* * * * *